(12) United States Patent
Leynov et al.

(10) Patent No.: US 10,993,731 B2
(45) Date of Patent: May 4, 2021

(54) SYSTEM AND METHOD FOR TREATING ISCHEMIC STROKE

(71) Applicant: Penumbra, Inc., Alameda, CA (US)

(72) Inventors: Aleksandr Leynov, Walnut Creek, CA (US); David Barry, San Ramon, CA (US); Vikas Gupta, San Leandro, CA (US); Arani Bose, New York, NY (US)

(73) Assignee: Penumbra, Inc., Alameda, CA (US)

( * ) Notice: Subject to any disclaimer, the term of this patent is extended or adjusted under 35 U.S.C. 154(b) by 289 days.

(21) Appl. No.: 15/488,349

(22) Filed: Apr. 14, 2017

(65) Prior Publication Data

US 2017/0215902 A1    Aug. 3, 2017

Related U.S. Application Data

(62) Division of application No. 13/253,242, filed on Oct. 5, 2011, now Pat. No. 9,655,633.

(51) Int. Cl.
| | |
|---|---|
| *A61B 17/221* | (2006.01) |
| *A61B 17/22* | (2006.01) |
| *A61B 17/00* | (2006.01) |
| *A61F 2/01* | (2006.01) |
| *A61M 25/10* | (2013.01) |

(52) U.S. Cl.
CPC ............ *A61B 17/221* (2013.01); *A61B 17/22* (2013.01); *A61B 2017/00526* (2013.01); *A61B 2017/2215* (2013.01); *A61B 2017/22034* (2013.01); *A61B 2017/22044* (2013.01); *A61B 2217/005* (2013.01); *A61F 2/013* (2013.01); *A61M 2025/1052* (2013.01); *Y10T 29/49826* (2015.01)

(58) Field of Classification Search
CPC .................. A61B 17/221; A61B 17/22; A61B 2017/00526; A61B 2017/22044; A61B 2017/2215; A61B 2217/005; A61B 2017/22034; A61M 2025/1052; A61F 2/013
See application file for complete search history.

(56) References Cited

U.S. PATENT DOCUMENTS

| | | | |
|---|---|---|---|
| 4,046,150 | A | 9/1977 | Schwartz et al. |
| 4,611,594 | A | 9/1986 | Grayhack et al. |
| 4,619,246 | A | 10/1986 | Molgaard-Nielsen et al. |
| 4,643,184 | A | 2/1987 | Mobin-Uddin |
| 4,706,671 | A | 11/1987 | Weinrib |
| 4,729,763 | A | 3/1988 | Henrie |
| 4,784,636 | A | 11/1988 | Rydell |
| 4,790,812 | A | 12/1988 | Hawkins, Jr. et al. |

(Continued)

FOREIGN PATENT DOCUMENTS

| | | |
|---|---|---|
| CN | 101020074 A | 8/2007 |
| CN | 101415380 A | 4/2009 |

(Continued)

OTHER PUBLICATIONS

European search report and opinion dated Apr. 24, 2015 for EP Application 12838884.
International search report and written opinion dated Apr. 12, 2006 for PCT/US2005/030402.
International search report and written opinion dated Dec. 6, 2012 for PCT/US2012/058695.

(Continued)

*Primary Examiner* — Ryan J. Walters
(74) *Attorney, Agent, or Firm* — Haley Guiliano LLP

(57) ABSTRACT

A thromboembolic removal system for treating ischemic stroke, including a guide and occlusion catheter, a delivery and aspiration catheter, an aspiration pump, a thromboembolic receiver, and a thromboembolic separator.

7 Claims, 35 Drawing Sheets

(56) References Cited

U.S. PATENT DOCUMENTS

| | | |
|---|---|---|
| 4,867,141 A | 9/1989 | Nakada et al. |
| 4,870,953 A | 10/1989 | Donmicheal et al. |
| 4,873,978 A | 10/1989 | Ginsburg |
| 4,898,575 A | 2/1990 | Fischell et al. |
| 4,927,426 A | 5/1990 | Dretler |
| 4,979,939 A | 12/1990 | Shiber |
| 4,990,134 A | 2/1991 | Auth et al. |
| 5,011,488 A | 4/1991 | Ginsburg |
| 5,024,651 A | 6/1991 | Shiber |
| 5,047,040 A | 9/1991 | Simpson et al. |
| 5,069,664 A | 12/1991 | Guess et al. |
| 5,100,423 A | 3/1992 | Fearnot |
| 5,100,424 A | 3/1992 | Jang et al. |
| 5,133,733 A | 7/1992 | Rasmussen et al. |
| 5,135,483 A | 8/1992 | Wagner et al. |
| 5,176,687 A | 1/1993 | Hasson et al. |
| 5,190,561 A | 3/1993 | Graber |
| 5,195,954 A | 3/1993 | Schnepp-Pesch et al. |
| 5,248,296 A | 9/1993 | Alliger |
| 5,273,526 A | 12/1993 | Dance et al. |
| 5,324,304 A | 6/1994 | Rasmussen |
| 5,380,273 A | 1/1995 | Dubrul et al. |
| 5,395,390 A | 3/1995 | Simon et al. |
| 5,417,697 A | 5/1995 | Wilk et al. |
| 5,423,830 A | 6/1995 | Schneebaum et al. |
| 5,476,450 A | 12/1995 | Ruggio |
| 5,501,694 A | 3/1996 | Ressemann et al. |
| 5,522,819 A | 6/1996 | Graves et al. |
| 5,549,626 A | 8/1996 | Miller et al. |
| 5,634,897 A | 6/1997 | Dance et al. |
| 5,643,297 A | 7/1997 | Nordgren et al. |
| 5,695,507 A | 12/1997 | Auth et al. |
| 5,746,758 A | 5/1998 | Nordgren et al. |
| 5,792,145 A | 8/1998 | Bates et al. |
| 5,800,519 A | 9/1998 | Sandock |
| 5,827,229 A | 10/1998 | Auth et al. |
| 5,843,103 A | 12/1998 | Wulfman |
| 5,911,733 A | 6/1999 | Parodi |
| 5,938,645 A | 8/1999 | Gordon |
| 5,972,019 A | 10/1999 | Engelson et al. |
| 6,001,112 A | 12/1999 | Taylor |
| 6,013,093 A | 1/2000 | Nott et al. |
| 6,066,149 A | 5/2000 | Samson et al. |
| 6,068,645 A | 5/2000 | Tu |
| 6,083,259 A | 7/2000 | Frantzen |
| 6,123,715 A | 9/2000 | Amplatz |
| 6,152,932 A | 11/2000 | Ternstroem |
| 6,156,048 A | 12/2000 | Wulfman et al. |
| 6,156,055 A | 12/2000 | Ravenscroft |
| 6,165,199 A | 12/2000 | Barbut |
| 6,168,603 B1 | 1/2001 | Leslie et al. |
| 6,203,561 B1 | 3/2001 | Ramee et al. |
| 6,224,612 B1 | 5/2001 | Bates et al. |
| 6,306,163 B1 | 10/2001 | Fitz |
| 6,350,266 B1 | 2/2002 | White et al. |
| 6,350,271 B1 | 2/2002 | Kurz et al. |
| 6,361,545 B1 | 3/2002 | Macoviak et al. |
| 6,383,196 B1 | 5/2002 | Leslie et al. |
| 6,383,205 B1 | 5/2002 | Samson et al. |
| 6,402,771 B1 | 6/2002 | Palmer et al. |
| 6,443,966 B1 | 9/2002 | Shiu |
| 6,443,972 B1 | 9/2002 | Bosma et al. |
| 6,458,139 B1 | 10/2002 | Palmer et al. |
| 6,482,217 B1 | 11/2002 | Pintor et al. |
| 6,506,166 B1 | 1/2003 | Hendler et al. |
| 6,511,492 B1 | 1/2003 | Rosenbluth et al. |
| 6,514,273 B1 | 2/2003 | Voss et al. |
| 6,517,551 B1 | 2/2003 | Driskill |
| 6,517,574 B1 | 2/2003 | Chuter |
| 6,530,923 B1 | 3/2003 | Dubrul et al. |
| 6,544,276 B1 | 4/2003 | Azizi |
| 6,551,327 B1 | 4/2003 | Dhindsa |
| 6,551,342 B1 | 4/2003 | Shen et al. |
| 6,575,997 B1 | 6/2003 | Palmer et al. |
| 6,589,263 B1 | 7/2003 | Hopkins et al. |
| 6,592,607 B1 | 7/2003 | Palmer et al. |
| 6,602,204 B2 | 8/2003 | Dubrul et al. |
| 6,610,077 B1 | 8/2003 | Hancock et al. |
| 6,616,676 B2 | 9/2003 | Bashiri et al. |
| 6,629,953 B1 | 10/2003 | Boyd |
| 6,660,014 B2 | 12/2003 | Demarais et al. |
| 6,660,021 B1 | 12/2003 | Palmer et al. |
| 6,666,874 B2 | 12/2003 | Heitzmann et al. |
| 6,685,722 B1 | 2/2004 | Rosenbluth et al. |
| 6,692,504 B2 | 2/2004 | Kurz et al. |
| 6,702,834 B1 | 3/2004 | Boylan et al. |
| 6,709,465 B2 | 3/2004 | Mitchell et al. |
| 6,719,717 B1 | 4/2004 | Johnson et al. |
| 6,726,702 B2 | 4/2004 | Khosravi |
| 6,761,727 B1 | 7/2004 | Ladd |
| 6,800,080 B1 | 10/2004 | Bates |
| 6,808,531 B2 | 10/2004 | Lafontaine et al. |
| 6,881,218 B2 | 4/2005 | Beyer et al. |
| 6,929,634 B2 | 8/2005 | Dorros et al. |
| 6,939,361 B1 | 9/2005 | Kleshinski |
| 6,942,673 B2 | 9/2005 | Bates et al. |
| 6,964,672 B2 | 11/2005 | Brady et al. |
| 7,063,707 B2 | 6/2006 | Bose et al. |
| 7,128,718 B2 | 10/2006 | Hojeibane et al. |
| 7,169,154 B1 | 1/2007 | Que et al. |
| 7,179,275 B2 | 2/2007 | McGuckin et al. |
| 7,195,648 B2 | 3/2007 | Jones et al. |
| 7,241,304 B2 | 7/2007 | Boyle et al. |
| 7,316,692 B2 | 1/2008 | Huffmaster |
| 7,329,269 B2 | 2/2008 | Shapiro et al. |
| 7,384,407 B2 | 6/2008 | Rodriguez et al. |
| 7,686,825 B2 | 3/2010 | Hauser et al. |
| 7,931,659 B2 | 4/2011 | Bose et al. |
| 8,257,428 B2 | 9/2012 | Khairkhahan et al. |
| 8,262,689 B2 | 9/2012 | Boyle et al. |
| 8,282,668 B2 | 10/2012 | McGuckin et al. |
| 8,460,312 B2 | 6/2013 | Bose et al. |
| 8,591,540 B2 | 11/2013 | Boyle et al. |
| 8,852,205 B2 | 10/2014 | Brady et al. |
| 9,119,656 B2 | 9/2015 | Bose et al. |
| 9,655,633 B2 | 5/2017 | Leynov et al. |
| 2001/0051810 A1 | 12/2001 | Dubrul et al. |
| 2002/0010487 A1 | 1/2002 | Evans et al. |
| 2002/0019597 A1 | 2/2002 | Dubrul et al. |
| 2002/0022859 A1 | 2/2002 | Hogendijk |
| 2002/0072764 A1 | 6/2002 | Sepetka et al. |
| 2002/0147459 A1 | 10/2002 | Bashiri et al. |
| 2002/0151906 A1 | 10/2002 | Demarais et al. |
| 2003/0018355 A1 | 1/2003 | Goto et al. |
| 2003/0040762 A1 | 2/2003 | Dorros et al. |
| 2003/0050663 A1 | 3/2003 | Khachin et al. |
| 2003/0055445 A1 | 3/2003 | Evans et al. |
| 2003/0078605 A1 | 4/2003 | Bashiri et al. |
| 2003/0078606 A1 | 4/2003 | Lafontaine et al. |
| 2003/0088235 A1 | 5/2003 | Tazi |
| 2003/0130685 A1 | 7/2003 | Daniel et al. |
| 2003/0150821 A1 | 8/2003 | Bates et al. |
| 2003/0153944 A1 | 8/2003 | Phung et al. |
| 2003/0163158 A1 | 8/2003 | White |
| 2003/0181827 A1 | 9/2003 | Hojeibane et al. |
| 2003/0195554 A1 | 10/2003 | Shen et al. |
| 2003/0208253 A1 | 11/2003 | Beyer et al. |
| 2003/0212430 A1 | 11/2003 | Bose et al. |
| 2003/0217794 A1 | 11/2003 | Boylan et al. |
| 2004/0068288 A1 | 4/2004 | Palmer et al. |
| 2004/0082967 A1 | 4/2004 | Broome et al. |
| 2004/0138692 A1 | 7/2004 | Phung et al. |
| 2004/0236350 A1 | 11/2004 | Lewis et al. |
| 2005/0038447 A1 | 2/2005 | Huffmaster |
| 2005/0055034 A1 | 3/2005 | Bates |
| 2005/0055047 A1 | 3/2005 | Greenhalgh |
| 2005/0059993 A1 | 3/2005 | Ramzipoor et al. |
| 2005/0288705 A1 | 12/2005 | Gilson et al. |
| 2006/0058836 A1 | 3/2006 | Bose et al. |
| 2006/0058837 A1 | 3/2006 | Bose et al. |
| 2006/0058838 A1 | 3/2006 | Bose et al. |
| 2007/0198028 A1 | 8/2007 | Miloslavski et al. |
| 2007/0208370 A1 | 9/2007 | Hauser et al. |
| 2008/0269774 A1 | 10/2008 | Garcia et al. |

(56) References Cited

U.S. PATENT DOCUMENTS

| | | |
|---|---|---|
| 2009/0105747 A1 | 4/2009 | Chanduszko et al. |
| 2009/0299393 A1 | 12/2009 | Martin et al. |
| 2010/0100106 A1 | 4/2010 | Ferrera |
| 2010/0185230 A1 | 7/2010 | Horan et al. |
| 2010/0211094 A1 | 8/2010 | Sargent, Jr. |
| 2010/0217276 A1 | 8/2010 | Garrison et al. |
| 2010/0256600 A1 | 10/2010 | Ferrera |
| 2011/0160761 A1 | 6/2011 | Ferrera et al. |
| 2011/0172700 A1 | 7/2011 | Bose et al. |
| 2011/0184456 A1 | 7/2011 | Grandfield et al. |
| 2011/0224707 A1 | 9/2011 | Miloslavski et al. |
| 2012/0116440 A1 | 5/2012 | Leynov et al. |
| 2014/0155931 A1 | 6/2014 | Bose et al. |
| 2014/0277082 A1 | 9/2014 | Janardhan et al. |

FOREIGN PATENT DOCUMENTS

| | | |
|---|---|---|
| DE | 2729566 A1 | 1/1979 |
| WO | WO-0197697 A1 | 12/2001 |
| WO | WO-03011188 A1 | 2/2003 |
| WO | WO-03075793 A1 | 9/2003 |
| WO | WO-2006031410 A2 | 3/2006 |
| WO | WO-2011095352 A1 | 8/2011 |
| WO | WO-2012120490 A2 | 9/2012 |
| WO | WO-2013052625 A1 | 4/2013 |

OTHER PUBLICATIONS

Office action dated May 7, 2015 for U.S. Appl. No. 13/253,242.
Office Action dated Aug. 2, 2016 for U.S. Appl. No. 13/253,242.
Office action dated Oct. 22, 2015 for U.S. Appl. No. 13/253,242.
Office action dated Oct. 24, 2014 for U.S. Appl. No. 13/253242..

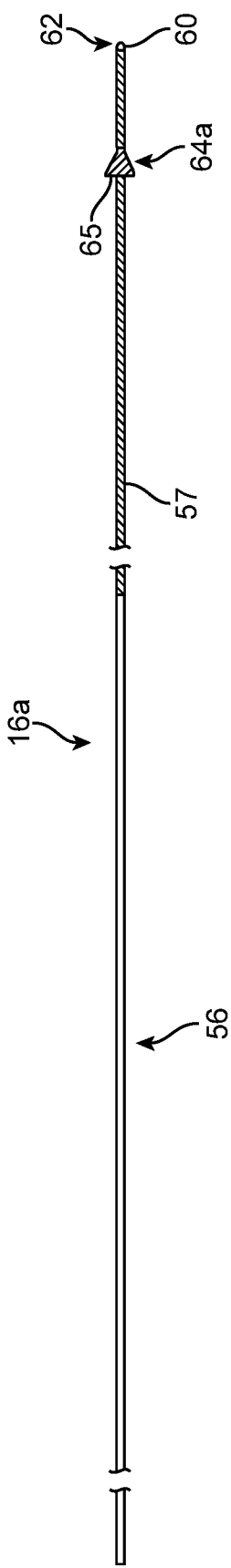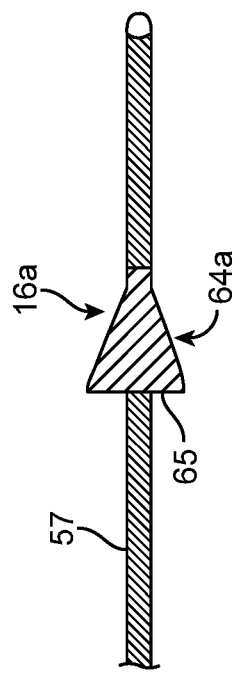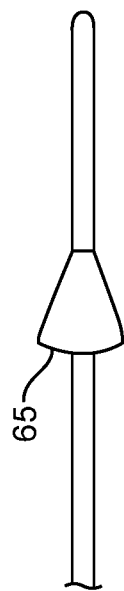
FIG. 11B
FIG. 11C
FIG. 11D

SYSTEM AND METHOD FOR TREATING ISCHEMIC STROKE

CROSS-REFERENCE TO RELATED APPLICATIONS

This application is a divisional of U.S. patent application Ser. No. 13/253,242, filed Oct. 5, 2011, now U.S. Pat. No. 9,655,633, the entire content of which are incorporated herein by reference.

FIELD OF THE INVENTION

The present invention relates generally to the field of medical treatment and, more particularly, to a system and method for treating ischemic stroke which involves removing a thromboembolism from a cerebral artery of a patient.

BACKGROUND

Stroke is a leading cause of death and disability and a growing problem to global healthcare. In the US alone, over 700,000 people per year suffer a major stroke and, of these, over 150,000 people die. Even more disturbing, this already troubling situation is expected to worsen as the "baby boomer" population reaches advanced age, particularly given the number of people suffering from poor diet, obesity and/or other contributing factors leading to stroke. Of those who a survive stroke, approximately 90% will suffer long term impairment of movement, sensation, memory or reasoning, ranging from mild to severe. The total cost to the US healthcare system is estimated to be over $50 billion per year.

Strokes may be caused by a rupture of a cerebral artery ("hemorrhagic stroke") or a blockage in a cerebral artery due to a thromboembolism ("ischemic stroke"). A thromboembolism is a detached blood clot that travels through the bloodstream and lodges in a manner that obstructs or occludes a blood vessel. Between the two types of strokes, ischemic stroke comprises the larger problem, with over 600,000 people in the US suffering with ischemic stroke per year.

Ischemic stroke treatment may be accomplished via pharmacological elimination of the thromboembolism and/or mechanical elimination of the thromboembolism. Pharmacological elimination may be accomplished via the administration of thrombolytics (e.g., streptokinase, urokinase, tissue plasminogen activator (TPA)) and/or anticoagulant drugs (e.g., heparin, warfarin) designed to dissolve and prevent further growth of the thromboembolism. Pharmacologic treatment is non-invasive and generally effective in dissolving the thromboembolism. Notwithstanding these generally favorable aspects, significant drawbacks exist with the use of pharmacologic treatment. One such drawback is the relatively long amount of time required for the thrombolytics and/or anticoagulants to take effect and restore blood flow. Given the time-critical nature of treating ischemic stroke, any added time is potentially devastating. Another significant drawback is the heightened potential of bleeding or hemorrhaging elsewhere in the body due to the thrombolytics and/or anticoagulants.

Mechanical elimination of thromboembolic material for the treatment of ischemic stroke has been attempted using a variety of catheter-based transluminal interventional techniques. One such interventional technique involves deploying a coil into a thromboembolism (e.g. via corkscrew action) in an effort to ensnare or envelope the thromboembolism so it can be removed from the patient. Although an improvement over pharmacologic treatments for ischemic stroke, such coil-based retrieval systems have only enjoyed modest success (approximately 55%) in overcoming ischemic stroke due to thromboembolic material slipping past or becoming dislodged by the coil. In the latter case, the dislodgement of thromboembolic material may lead to an additional stroke in the same artery or a connecting artery.

Another interventional technique involves deploying a basket or net structure distally (or downstream) from the thromboembolism in an effort to ensnare or envelope the thromboembolism so it can be removed from the patient. Again, although overcoming the drawbacks of pharmacologic treatment, this nonetheless suffers a significant drawback in that the act of manipulating the basket or net structure distally from the occluded segment without angiographic roadmap visualization of the vasculature increases the danger of damaging the vessel. In addition, removing the basket or net structure may permit if not cause thromboembolic material to enter into connecting arteries. As noted above, this may lead to an additional stroke in the connecting artery.

A still further interventional technique for treating ischemic stroke involves advancing a suction catheter to the thromboembolism with the goal of removing it via aspiration (i.e. negative pressure). Although generally safe, removal via aspiration is only effective with relatively soft thrombus-emboli. To augment the effectiveness of aspiration techniques, a rotating blade has been employed to sever or fragment the thromboembolism, which may thereafter be removed via the suction catheter. While this rotating blade feature improves the effectiveness of such an aspiration technique, it nonetheless increases the danger of damaging the vessel due to the rotating blade.

The foregoing interventional techniques, as well as others in the prior art, all suffer one or more drawbacks and are believed to be sub-optimal for treating ischemic stroke. The present invention is directed at overcoming, or at least improving upon, the disadvantages of the prior art.

When such an obstruction occurs in a cerebral vessel, the result is a stroke and potential cell death soon thereafter. The resulting symptoms of immobility and/or loss of function depend upon the location of the occlusion within the cerebrovasculature, and the severity of impact of ischemic stroke is directly related to the length of time blood flow is occluded in a particular cerebral vessel. Specifically, regardless of the means of complete removal of a thromboembolism, a common urgency remains: to restore blood flow through the vessel as soon as possible after occlusion in order to minimize cell death during the acute phase of stroke, (and/or during the initial treatment of a patient) while physicians determine the desired course of treatment for permanent and complete elimination of the embolism. It is an object of the invention herein to provide a means for temporarily restoring blood flow through a blocked cerebral vessel, prior to and/or during the procedures to more permanently and completely remove the blockage, and to permanently and completely remove the blockage. It is a further object of the invention to remove embolic material from the vessel. It is a further object of the invention to provide a device that can be readily tracked through the tortuous and fragile anatomy of the cerebrovasculature. It is a further object of the invention to provide a device that will load readily into a delivery catheter, will deploy readily within the cerebrovasculature at the site of an occlusion, and will be readily removable via the delivery catheter following restoration of sufficient blood flow. It is a further object of the invention to permit the delivery and deployment of additional therapies (such as, for example, disruption and aspiration of the embolism) during use of the device.

In a first aspect, the present invention provides a system for removing thromboembolic material from a blood vessel. The system includes an elongate catheter proportioned for insertion into a blood vessel, where the catheter has a lumen extending therethrough. An elongate member is mounted to extend and retract through the lumen, and an expandable and collapsible separator element is disposed at a distal end of the elongate member. The separate element comprises a plurality of uprights and a multiplicity of apexes extending between said uprights, wherein at least some of the uprights and a first group of apexes are disposed about a central longitudinal axis of the separator and a second group of the apexes extend inwardly toward the central longitudinal axis of the separator.

In a second aspect, the present invention provides a method of manufacture of a system for removal of thromboembolic material from a blood vessel. The method comprises the steps of cutting a plurality of uprights and apexes from a length of tubing to form a separator element adjoining some of the apexes to one another, and mounting said separator element to an elongate element.

In a third aspect, the present invention provides a method of removal of thromboembolic material from a blood vessel of a subject. The method comprises the steps of introducing into the vessel proximate the thromboembolic material an elongate member having an expandable and collapsible separator element disposed at a distal end of the elongate member. The separator element comprises a plurality of uprights and a multiplicity of apexes extending between said uprights, wherein at least some of the uprights and a first group of apexes are disposed about a central longitudinal axis of the separator and a second group of the apexes extend inwardly toward the central longitudinal axis of the separator.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 5 shows it opened and flattened into a sheet so that its features may be more easily viewed;

FIG. 11B is a side elevation view of an alternate embodiment of a thromboembolic separator.

FIG. 11C is an enlarged view of the separator element forming part of the thromboembolic separator shown in FIG. 11B.

FIG. 11D is a side elevation view similar to FIG. 11C showing another alternate embodiment of a thromboembolic separator.

FIG. 31 illustrates it opened, flattened, and with the ribs forming the engagement cages of FIGS. 29 and 30 detached from one another, so that the features are more easily viewed.

FIG. 34 illustrates it opened and flattened, and with the ribs forming the engagement cages detached, so that the features are more easily viewed.

FIG. 37 illustrates it opened and flattened, and with the ribs forming the engagement cages of FIGS. 35 and 36 unattached, so that the features are more easily viewed.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be routine undertaking for those of ordinary skill in the art having the benefit of this disclosure. The thromboembolic removal system disclosed herein boasts a variety of inventive features and components that warrant patent protection, both individually and in combination.

System Features

Figure 1:
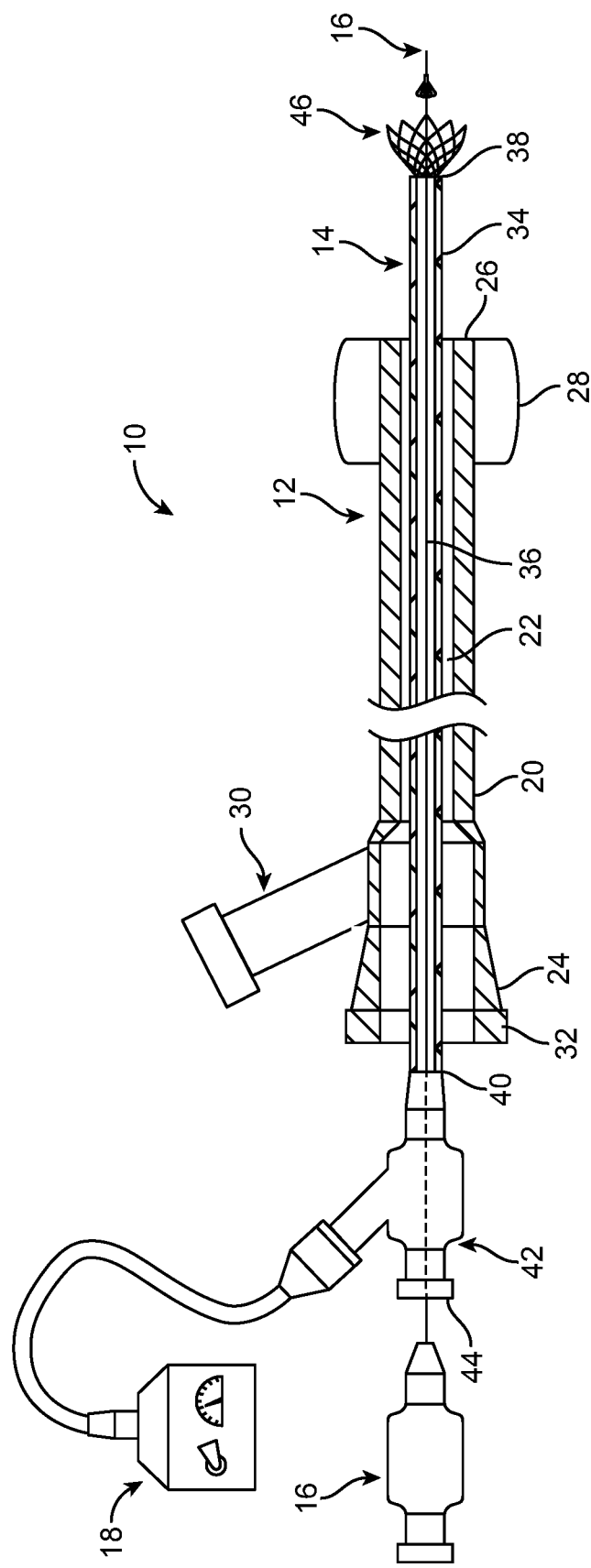
FIG. 1 is a partial sectional side view of one embodiment of a thromboembolic removal system, including a guide and occlusion catheter, a delivery and aspiration catheter, an aspiration pump, a thromboembolic receiver, and a thromboembolic separator.

FIG. 1 illustrates an exemplary embodiment of a thrombolic removal system 10. The thromboembolic removal system 10 includes a guide and occlusion catheter 12, a delivery and aspiration catheter 14, a thromboembolic disrupter or separator 16, and an aspiration pump 18. As will be described in greater detail below, the thromboembolic removal system 10 advantageously provides the ability to restore patency to and remove a thromboembolism from a cerebral artery within a patient while overcoming the drawbacks and limitations of the prior art.

The guide and occlusion catheter 12 includes a tubular catheter member 20 having a main lumen 22 extending between a proximal end 24 and a distal end 26. The catheter member 20 may be constructed from any number of compositions having suitable biocompatibility and strength characteristics, and may be dimensioned in any number of suitable sizes and lengths depending upon the entry point into the vasculature, the location of the thromboembolism, variances in patient anatomy, and any extenuating circumstances. In an exemplary embodiment, the catheter member 20 may be constructed from nylon with embedded stainless steel braid and dimensioned having a length ranging from 70 cm to 110 cm and a diameter ranging from 5 French (0.065 inch) to 9 French (0.117 inch). A balloon occlusion member 28 is disposed at or near the distal end 26. To selectively inflate the occlusion member 28, an inflation port 30 is provided in fluid communication with the occlusion member 28 via at least one lumen (not shown) disposed within the wall of the tubular catheter member 20. A seal 32 is provided for passing the delivery and aspiration catheter 14 through the main lumen 22 of the guide and occlusion catheter 12 in leak-free, hemostatic fashion.

The delivery and aspiration catheter 14 includes a tubular catheter element 34 having a main lumen 36 extending between a distal end 38 and a proximal end 40. The catheter member 34 may be constructed from any number of compositions having suitable biocompatibility and strength characteristics, and may be dimensioned in any number of suitable sizes and lengths depending upon the entry point into the vasculature, the location of the thromboembolism, variances in patient anatomy, and any extenuating circumstances. In an exemplary embodiment, the catheter member 34 may be constructed from pebax with embedded stainless steel braid and dimensioned having a length ranging from 130 cm to 170 cm and a diameter ranging from 2.5 French (0.032 inch) to 5 French (0.065 inch).

The delivery and aspiration catheter 14 also includes a hub assembly 42 coupled to the proximal end 40 for the purpose of coupling the lumen 36 to the aspiration pump 18. The hub assembly 42 also includes a seal 44 for allowing the passage of the thromboembolic separator 16 (as well as any pushing devices to deploy a receiver element 46, as will be discussed below) through the lumen 36 in leak-free, hemostatic fashion. The lumen is preferably coated with PTFE or another of the various suitable lubricious materials known in the art.

Figure 2:
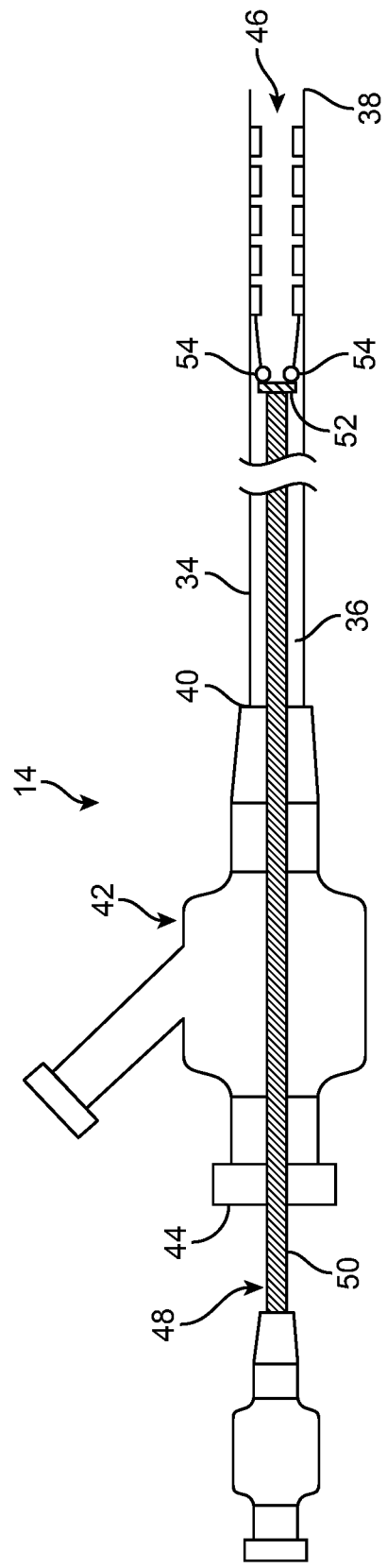
FIG. 2 is a partial sectional side view of a delivery and aspiration catheter forming part of the thromboembolic removal system shown in FIG. 1, illustrating a thromboembolic receiver element in an undeployed state.
Figure 3:
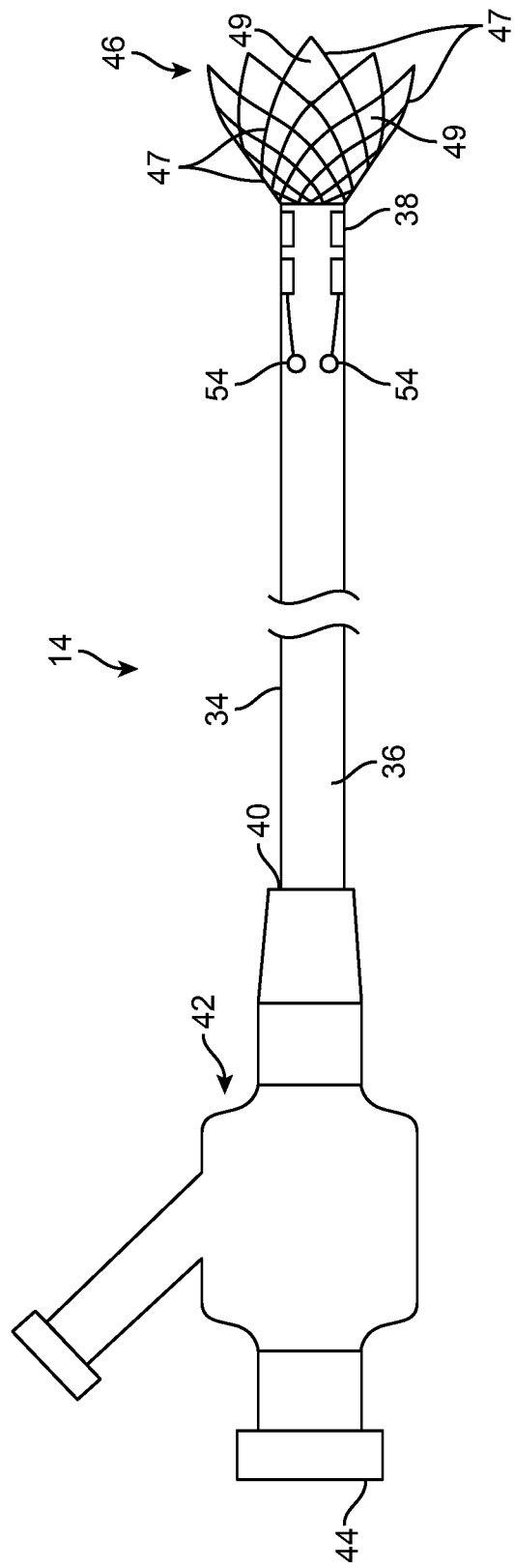
FIG. 3 is a partial sectional side view of a delivery and aspiration catheter forming part of the thromboembolic removal system shown in FIG. 1, illustrating the thromboembolic receiver element in a deployed state.

As best viewed with reference to FIGS. 2-3, the thromboembolic receiver element 46 is capable of being restrained in a withdrawn or undeployed state within the lumen 36 (FIG. 2) and selectively pushed out and/or unsheathed from the distal end 38 into a deployed state (FIG. 3). The thromboembolic receiver 46 may be constructed from any number of compositions having suitable biocompatibility and strength characteristics, and may be dimensioned in any number of suitable sizes and lengths depending upon the location of the thromboembolism, variances in patient anatomy, and the size and shape of the thromboembolism. As best viewed in FIGS. 3 and 5, the thromboembolic receiver 46 is formed from a plurality of strut members 47, which upon being deployed, create a multitude of generally diamond-shaped openings 49 along the periphery of the thromboembolic receiver 46. According to one embodiment, as shown in FIGS. 18-23, the resulting points at the distal region of the thromboembolic receiver 26 are equipped with blunt tip features 51 to facilitate passage of the thromboembolic receiver 46 through the cerebral artery without snagging or becoming otherwise stuck on the arterial walls or branch vessels leading into the cerebral artery.

A pusher element 48 may be provided within the catheter element 34 for use in advancing or pushing the receiver element 46 from within the lumen 36 to assume a fully or partially deployed state. By way of example only, the pusher element 48 comprises an elongate member 50 of suitable construction (e.g. wire or wire-wound) having a distal abutment 52 dimensioned to contact proximal terminal(s) 54 forming part of (or coupled to) the receiver element 46. Although not shown, it will be appreciated that the pusher element 48 may comprise any number of suitable devices for pushing the receiver element 46 for deployment, including but not limited to a catheter having a distal end dimensioned to contact the proximal terminal(s) 54 of the receiver element 46. In one embodiment, such a pusher-catheter may have an internally disposed lumen dimensioned to receive and/or pass the thromboembolic separator 16.

Figure 4A:
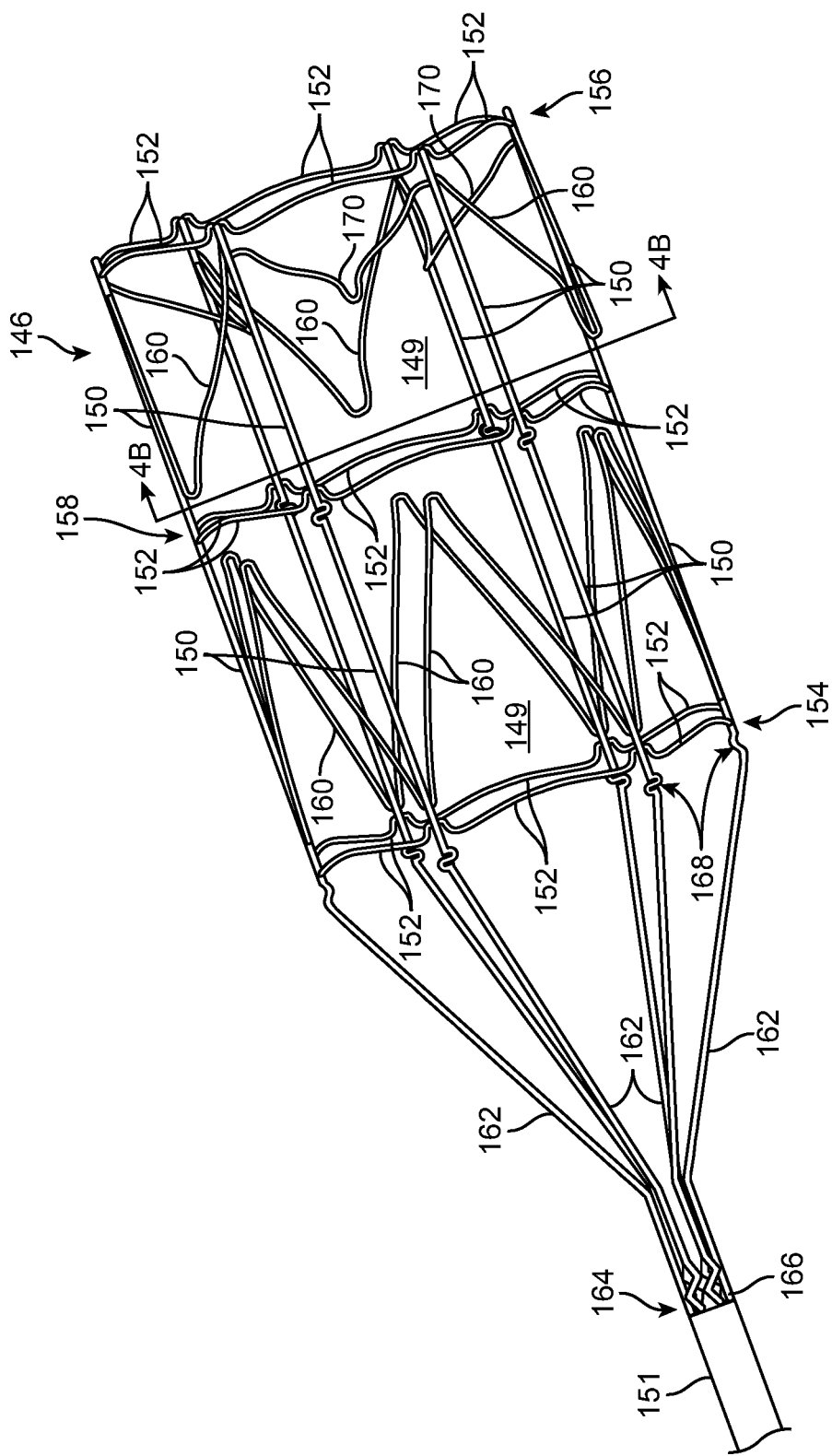
FIG. 4A is a perspective view depicting an alternate embodiment of a thromboembolic receiver, equipped with a plurality of engagement elements.

FIG. 4A illustrates a thromboembolic receiver 146 of an alternate embodiment. The thromboembolic receiver 146 may be constructed from any number of compositions having suitable biocompatibility and strength characteristics, and may be dimensioned in any number of suitable sizes and lengths depending upon the location of the thromboembolism, variances in patient anatomy, and the size and shape of the thromboembolism. In a preferred embodiment, the thromboembolic receiver 146 is constructed from Nitinol with "shape memory" or superelastic characteristics. In this fashion, the thromboembolic receiver 146 is capable of being retained in a constrained form or shape prior to deployment. The receiver may be formed by laser cutting features into a length of Nitinol tubing, and then chemically etching and shape-setting the material one or more times using methods known to those skilled in the art.

Referring to FIG. 4A, receiver 146 is mounted to an elongate member 151 preferably proportioned to extend through lumen 36 (FIG. 1) of the delivery and aspiration catheter 14. Strut members or "legs" 162 extend between receiver 146 and elongate member 151 using bonding, shrink tubing, or other known methods. In a preferred embodiment, member 151 is an elongate rod, catheter, wire or other elongate member. In this embodiment, the thromboembolic receiver 146 is proportioned so that it may be constrained in a compressed position within the delivery and aspiration catheter 14 (in a manner similar to that shown in FIGS. 1-3). Alternatively, the elongate member 151 may be the delivery and aspiration catheter 14, in which case the receiver 146 and delivery and aspiration catheter 14 are proportioned to extend through the guide and occlusion catheter 12.

In either event, the thromboembolic receiver 146 may be automatically deployed—due to the shape memory or superelastic characteristics of Nitinol—by simply advancing the thromboembolic receiver 146 out of the element constraining it in the undeployed state (e.g. the guide and occlusion catheter 12 or the delivery and aspiration catheter 14). Once deployed, the thromboembolic receiver 146 may be employed to retrieve a thromboembolism. The dimensions of the receiver 146 are preferably selected such that when it is in an expanded condition at body temperature, the exterior surface of the distal portion of the receiver contacts the surround walls of the blood vessel. In one embodiment suitable for more intracranial vessels, the receiver may expand to a maximum outer diameter of approximately 2-6 mm, and more preferably 2-5 mm. For other applications such as procedures within the common carotid artery, a maximum outer diameter in the range of approximately 6-9 mm may be suitable.

Figure 4B:
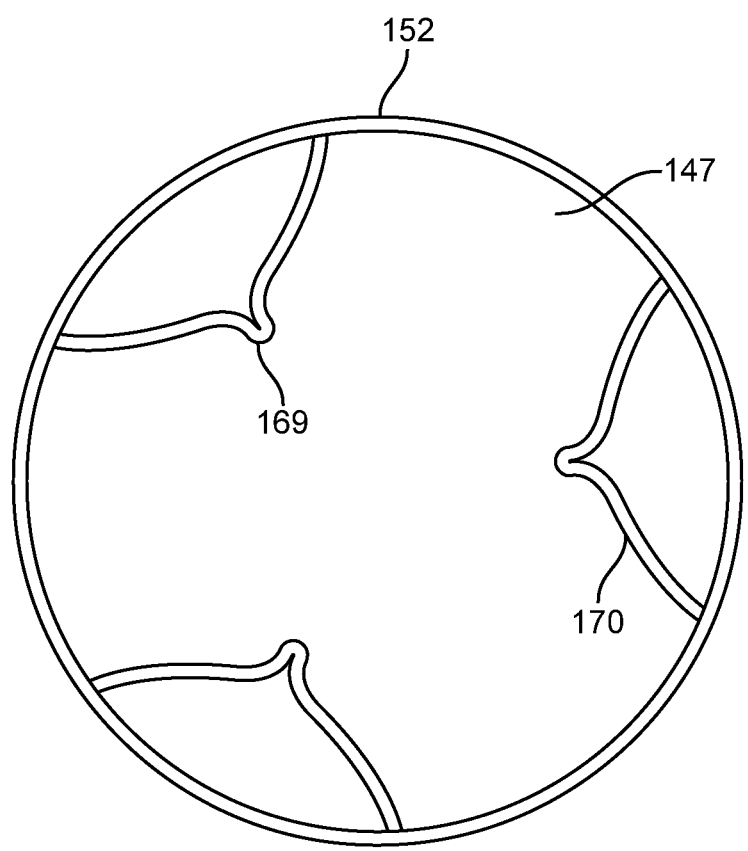
FIG. 4B is a cross section view taken along the plane designated 4B-4B in FIG. 4A.

The thromboembolic receiver 146 may be formed having any variety of suitable geometries and features without departing from the scope of the present invention. According to one embodiment shown in FIGS. 4A and 5, the thromboembolic receiver 146 is formed from a plurality of strut members, which upon being deployed, create a multitude of generally rectangular openings 149 (best viewed in FIG. 5) along the periphery of the thromboembolic receiver 146. This is accomplished, by way of example, by providing a plurality of longitudinal strut members or "standards" 150 (which are generally parallel to the longitudinal axis of the delivery and aspiration catheter 14), and a plurality of transverse strut members 152 (which extend generally perpendicularly between the adjacent standards). In a preferred embodiment, the strut members collectively define a generally cylindrical distal portion having a central lumen 147 as shown in FIG. 4B.

Figure 5:
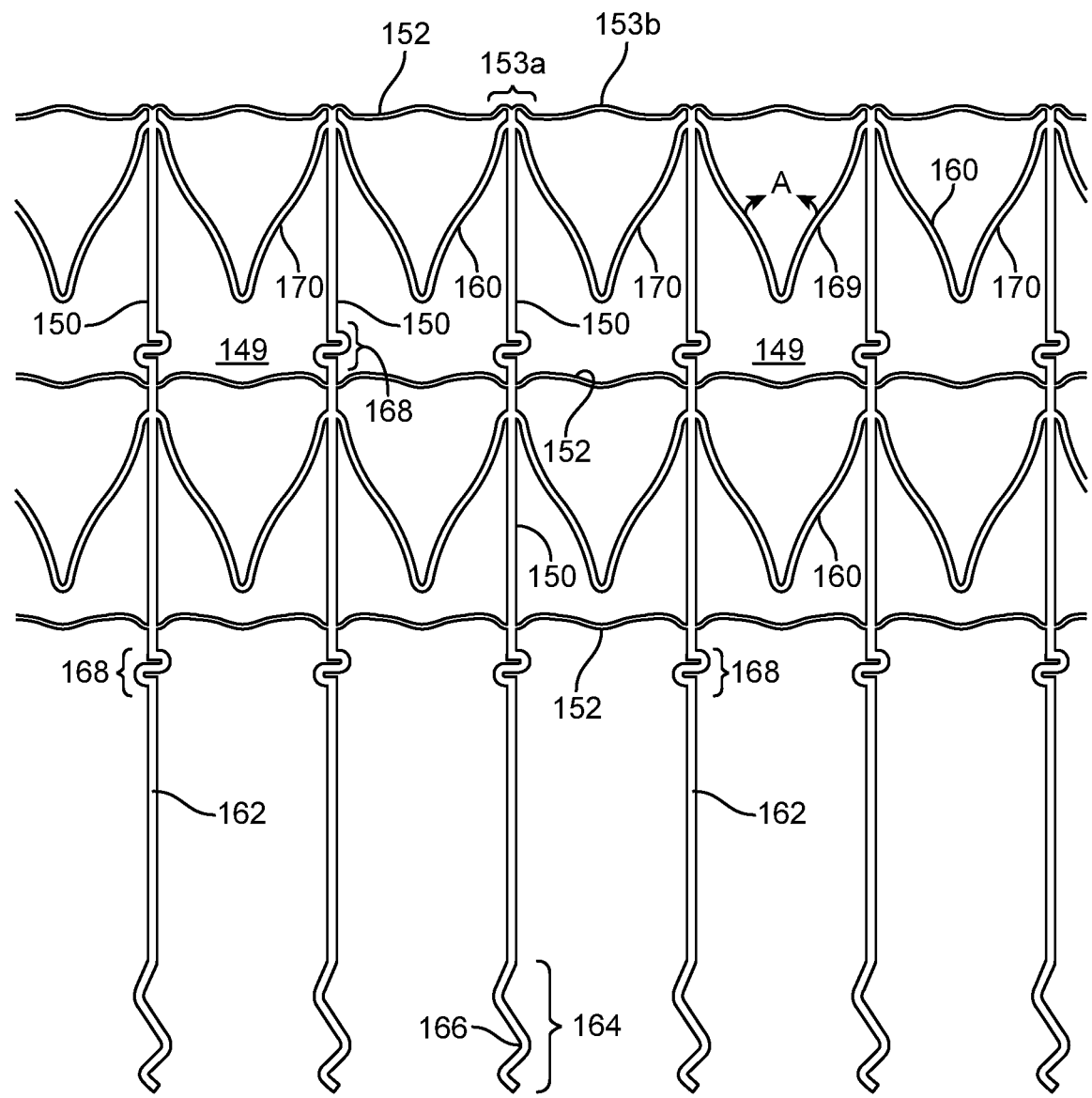
FIG. 5 is a plan view of the alternate thromboembolic receiver of FIG. 4. Although the receiver is preferably a tubular structure.

The transverse strut members 152 may include any number of curves or undulations, such as curves 153a shown near the points of intersection between the transverse strut members 152 and the standards 150, as well as the curves 153b midway between the points of intersection as shown in FIG. 5. Such curves or undulations help allow the thromboembolic receiver 146 to fold into a compressed or constrained state, which is required in order to dispose the thromboembolic receiver 146 within the delivery and aspiration catheter 14 or within the guide and occlusion catheter 12.

The transverse strut members 152 form, in a preferred embodiment, a proximal cuff 154 located closest to the delivery and aspiration catheter 14, a distal cuff 156 located at the distal or open end of the thromboembolic receiver 146, and a middle cuff 158 located at some point between the proximal and distal cuffs. Each cuff (proximal 154, middle 158, and distal 156) is a circumferential ring designed to enhance the structural support and stability of the thromboembolic receiver 146, as well as to aid in maintaining the thromboembolic receiver 146 in a desired shape upon deployment (for improved apposition to the vessel wall to optimize the thromboembolic retrieval).

The structural support provided by the cuffs 154-158 may be augmented by providing one or more stabilizing strut members 160 within one or more of the generally rectangular openings 149. According to one embodiment, these stabilizing strut members 160 may take the form of a "V" extending from either the proximal end or distal end of a given generally rectangular opening 149 within the thromboembolic receiver 146. In a preferred embodiment, such "V" shaped stabilizing strut members 160 are provided within the proximal and distal set of generally rectangular openings 149 within the thromboembolic receiver 146. This advantageously adds to the structural stability of the proximal and distal regions of the thromboembolic receiver 146. Regardless of their specific shape, the stabilizing strut members 160 preferably include folding regions or apexes 169 that allow them to fold at the apexes 169 (see arrows A in FIG. 5) when the receiver is compressed into the collapsed position. Additionally, the receiver is preferably constructed so as to permit the strut members 160 to fold in the region where they intersect with other elements forming the receiver (e.g. in the FIG. 5 embodiment, the region of intersection between strut members 160 and standards 150).

Figure 6:
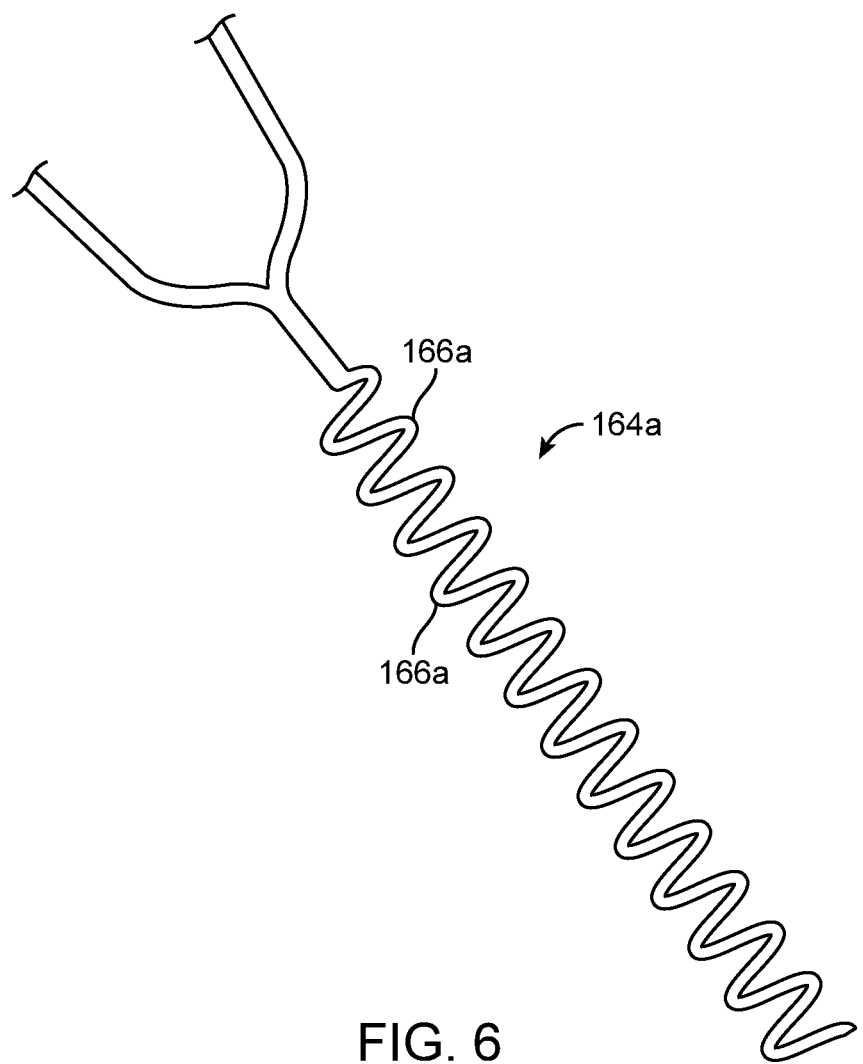
FIG. 6 is a top view illustrating one embodiment of a flex region for use in flexibly coupling the thromboembolic receiver, such as the receiver of FIG. 4A, to an elongate member or a delivery and aspiration catheter.

While structural stability of the thromboembolic receiver 146 is a desired goal, it is also desired to have certain aspects of flexibility. According to one embodiment, relative flexibility is provided at the junction between the thromboembolic receiver 146 and the elongate member 151 (or the distal end of the delivery and aspiration catheter 14). This is accomplished, by way of example only, by providing the plurality of connector strut members or "legs" 162 extending between the proximal cuff and the elongate member 151 to include (as best viewed in FIG. 5) a flex region 164 near the distal end of the elongate member 151. The flex regions 164 may be formed into any shape that will add flexibility to the strut members 162 without comprising the user's ability to transmit axial forces along the length of the strut members 162. In an alternate embodiment shown in FIG. 6, the flex regions 164a may comprise a plurality of meandering "S" shaped struts 166a at the proximal ends of the connector struts 162. According to another embodiment, a flex region or spring region 168 (FIG. 5) (which may comprise one of more "S" shaped curves or other shapes designed to provide flexibility while maintaining adequate column strength) may be provided at the junction between adjacent longitudinal strut members or standards 150. In both instances, such flex regions 164, 168 are advantageous in that they allow the thromboembolic receiver 146 to better track and follow tortuous vessels without sacrificing needed column strength.

Figure 4C:
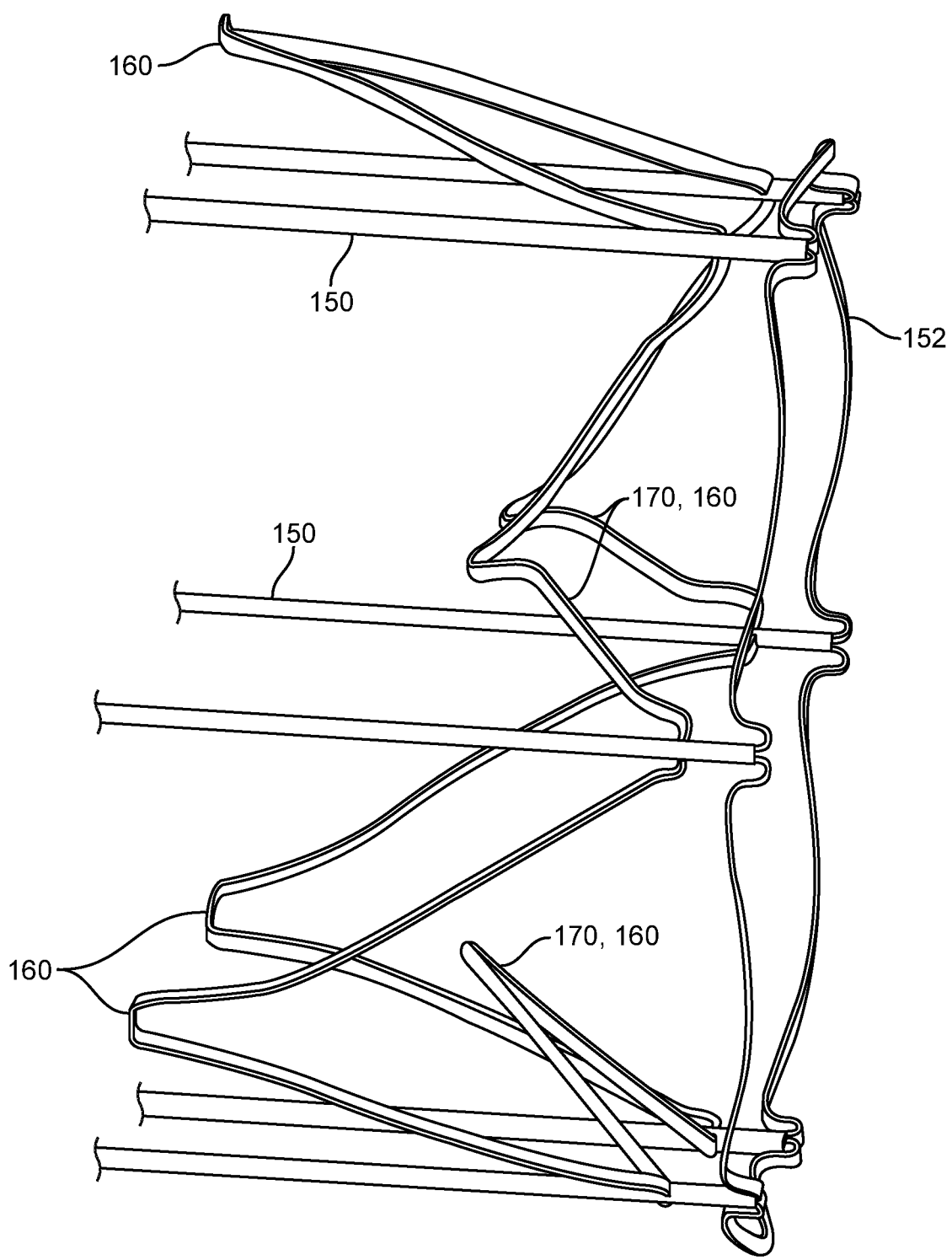
FIG. 4C is a perspective view illustrating the distal portion of the thromboembolic receiver of FIG. 4A.

According to a further embodiment, the thromboembolic receiver 146 may also include a variety of features to augment engagement between the thromboembolic receiver 146 and the thromboembolism. This may be accomplished, by way of example only, by providing a plurality of engagement elements 170 on the thromboembolic receiver. As best viewed in FIGS. 4A, 4B and 5, the engagement elements 170 may, according to one embodiment, take the form of a "V" shaped structure coupled at or near the distal end of the thromboembolic receiver 146 and extending between adjacent standards 150. The engagement elements preferably angle into the lumen 147 of the thromboembolic receiver (see FIGS. 4B and 4C) so as to permit engagement of a thromboembolism captured within the lumen. Any number of engagement elements 170 may be employed without departing from the scope of the present invention. In one embodiment, three (3) separate engagement elements 170 may be employed, each being disposed one hundred and twenty (120) degrees from one another along the periphery of the thromboembolic receiver 146. In a preferred embodiment, the engagement elements 170 take the form of a plurality of the stabilizing strut members 160 as shown in FIGS. 4A and 5.

Figure 7:
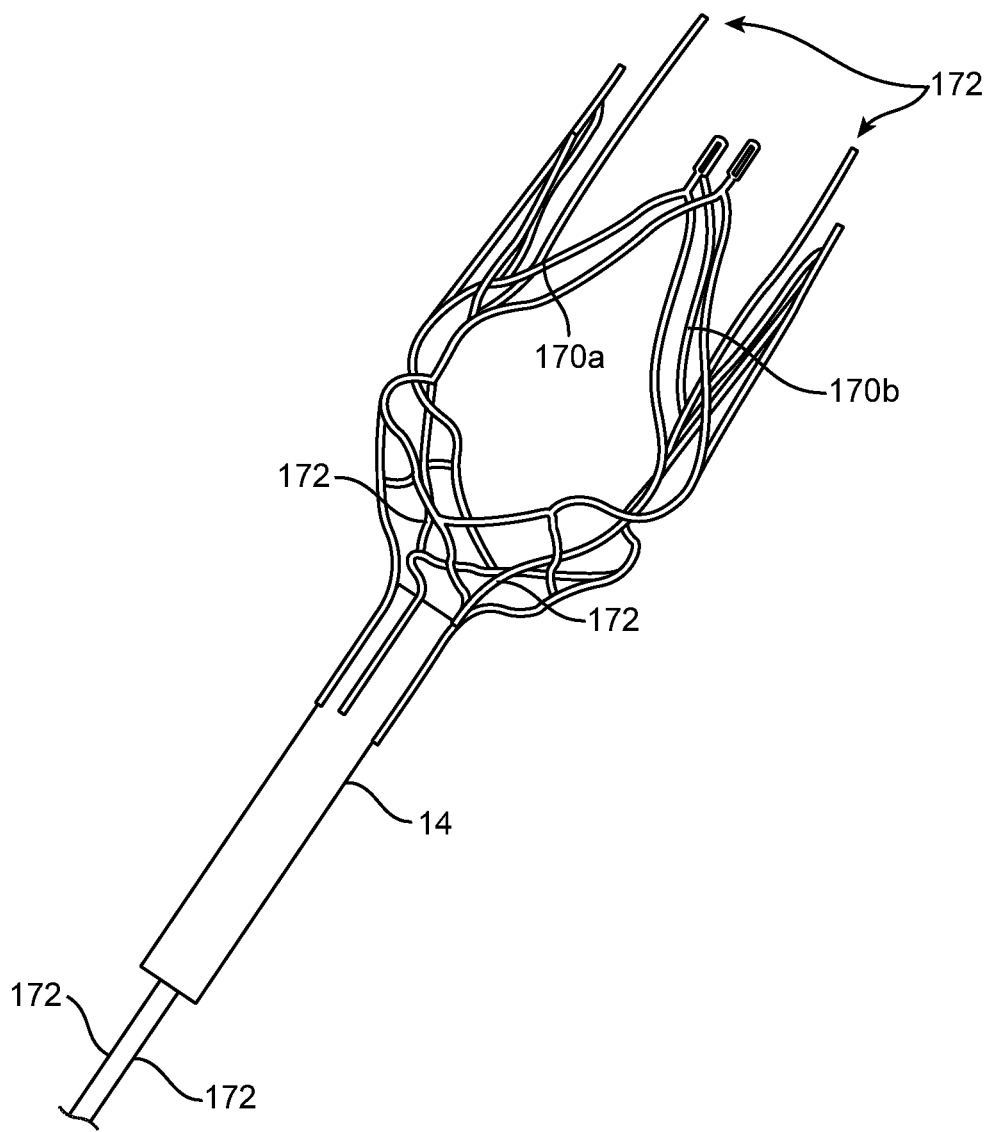
FIG. 7 is a perspective view of an alternate thromboembolic receiver, equipped with a plurality of engagement elements capable of being selectively deployed after the deployment of the thromboembolic receiver.

The engagement elements 170 may be deployed automatically when the thromboembolic receiver 146 is deployed (as shown in FIG. 4-5). In accordance with another aspect of the invention shown in FIG. 7, the engagement elements 170a may also be selectively deployed at any point following the deployment of the thromboembolic receiver 146a. According to the FIG. 7 embodiment, the selective deployment of the engagement elements 170a is accomplished by passing one or more elongate elements 172 through the thromboembolic receiver 146a such that the engagement elements 170a are prevented from extending medially into the lumen of the thromboembolic receiver 146. When deployment is desired, a user need only pull the elongate elements 172 in a proximal direction (towards the user) until the engagement elements 170a are set free from the constraint of the elongate elements 172. When this occurs, the "shape memory" or superelastic nature of the engagement elements 170a will cause them to assume their natural state, extending medially into the lumen of the thromboembolic receiver 146a. In this fashion, the engagement elements 170a will engage the thromboembolism and thus aid or enhance the ability of the thromboembolic receiver 146a to remove a thromboembolism.

The thromboembolic receiver may be provided with features that allow a surgeon to retract the receiver back into the delivery and aspiration catheter after the receiver has been partially or fully deployed into a blood vessel. This might be necessary if, perhaps, the surgeon receives angiographic or tactile feedback indicating that a separator would be a preferred tool for removal of a particular embolism, or that a receiver of a different size would be more suitable for a particular procedure.

Figure 8:
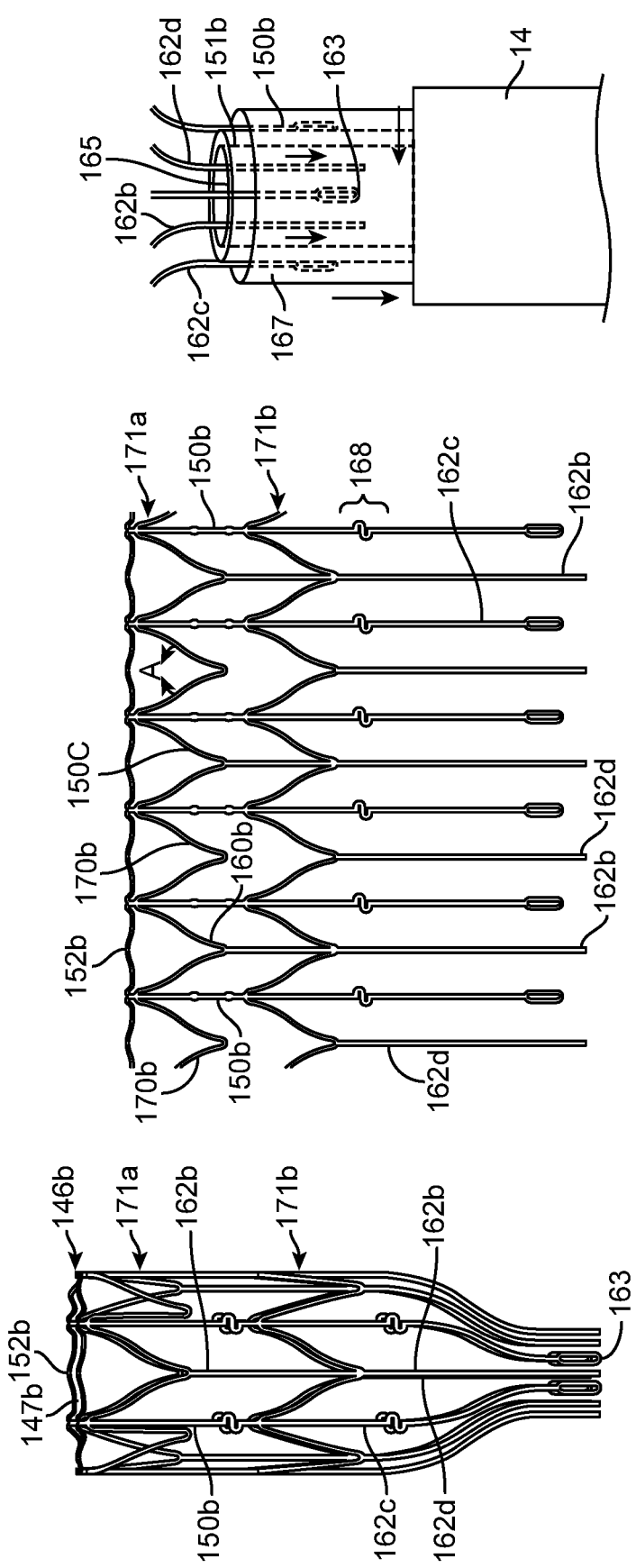
FIG. 8A is perspective view of a thromboembolic receiver having features for facilitating reloading of the receiver into a catheter.
FIG. 8B is a plan view similar to the view of FIG. 5 showing the thromboembolic receiver of FIG. 8A.
FIG. 8C is a perspective view of a proximal portion of the thromboembolic receiver of FIG. 8A and the distal portion of the elongate member coupled to the thromboembolic receiver, illustrating retraction of the thromboembolic receiver into a delivery and aspiration catheter.

FIG. 8A illustrates one example of an embodiment of a thromboembolic receiver 146b that is similar to the receiver 146 of FIG. 4, but that includes the features that facilitate reloading of the receiver into the delivery and aspiration catheter 14. As shown, receiver 146b of the FIG. 8A embodiment includes a single, distal, cuff 152b and a plurality of longitudinal strut members 150b extending proximally from the cuff 152b.

Structural support members 160b are arranged in a distal row 171a adjacent to the cuff 152b, and a more proximal row 171b as shown in FIG. 8B. As with the FIG. 4 embodiment, a plurality of the structural support members 160b in the distal row are inwardly biased into the central lumen 147b of the receiver 146b so as to function as engagement members 170b for engaging a thromboembolism.

Three types of stabilizing strut members extend towards the proximal end of the receiver 146b. First, strut members 162b extend distally from the apexes of those of the structural support members 160b in the distal row 171a that do not function as engagement members. These strut members 162b are coupled at an intermediate point to the apexes of longitudinally aligned support members 160b in the proximal row. Second, strut members 162c form the proximal extensions of the longitudinal strut members 150b and include eyelets 163 at their proximal ends. Third, strut members 162d extend from the apexes of those of the structure support members 160b in the proximal row that are longitudinally aligned with the engagement members 170b. Flexibility may be added to the receiver 146b may constructing some or all of the strut members to include flex regions of the type described in connection with earlier embodiments (see, e.g. flex regions 168 of FIG. 5).

Referring to FIG. 8C, the receiver 146b includes a pusher or elongate member 151b that includes a lumen 165 at its distal end. During assembly of the receiver 146b, the proximal ends of strut members 162b and 162d are positioned within the lumen 165 as shown and are allowed to slide freely within the lumen 165. The proximal ends of strut members 162c are bonded to the exterior surface of the elongate member 151b using heat shrink tubing 167 or other suitable material. The eyelets 163 facilitate bonding by allowing the bonding material to flow into the openings of the eyelets, thereby exposing a larger portion of each strut member 162c to the bonding material. If desired, the strut members 162b and 162d may be somewhat longer than the strut members 162c at the proximal end of the receiver, to allow them to be easily identified for insertion into the lumen 165 during assembly.

If it should be necessary to withdraw the receiver 146b back into the delivery and aspiration catheter 14 from a fully or partially deployed state, the elongate member 151b is withdrawn in a proximal direction relative to the catheter as shown in FIG. 8C. As the receiver 146b moves into the catheter 14, the receiver begins to fold at the apexes of the structural support members 162b and 162d in a proximal direction. Folding is more easily accomplished than with the receiver 146 of FIG. 4 due to the fact that certain of the structural support members 160b are interconnected at their apexes by strut members 162b. Thus, the folding of one member 160b in the proximal row 171b will facilitate the folding of a corresponding member 160b in the distal row 171a. The strut members 162b and 162d are allowed to slide freely within the lumen 165 of the elongate member 151b so that they will not resist folding of the members 160b during withdrawal of the receiver 146b into the catheter 14.

Figure 9:
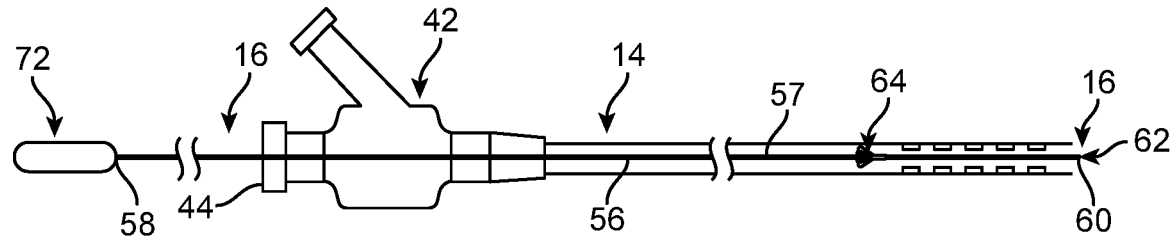
FIGS. 9 and 10 are partial sectional side views of one embodiment of a thromboembolic disrupter or separator in use with a delivery and aspiration catheter.

A first embodiment of a thromboembolic separator is shown in FIG. 9. The thromboembolic separator 16 of the first embodiment includes an elongated element 56 having a proximal end 58 and a distal end 60. The elongated element 56 may be constructed from any number of compositions having suitable biocompatibility and strength characteristics, and may be dimensioned in any number of suitable sizes and lengths depending upon the entry point in vasculature, the location of the thromboembolism, variances in patient anatomy, and any extenuating circumstances. In an exemplary embodiment, the elongated element 56 may be constructed from stainless steel and/or Nitinol and dimensioned having a length ranging from 150 cm to 200 cm and a diameter ranging from 0.010 inch to 0.021 inch. A lubricious surface (e.g., a PTFE coating, hydrophilic coating, or other suitable coatings) may be applied to all or a portion of the elongate element 56 to facilitate movement of the element within the lumen of the delivery/aspiration catheter 14 and/or within the vasculature.

If desired, the elongate element 56 may take the form of a guide wire of the type used in various vascular applications. The elongate element may thus optionally include a coiled distal section 57 (FIG. 11B) having sufficient flexibility to prevent trauma to vascular tissues during advancement of the guidewire. In an exemplary embodiment, coiled distal section 57 may have a length in the range of approximately 27-33 cm. The coil is preferably positioned around an inner mandrel or core (not shown) of a type commonly found in coiled guidewires.

The "working end" of the separator 16 includes a generally blunt tip element 62 attached or forming part of the distal end 60 of the elongated element 56, and a separator element 64 attached or forming part of the elongated element 56. The tip element 62 is preferably dimensioned to pass through or against a thromboembolism so as to soften or fragment the thromboembolism for removal. The blunt nature of the tip element 62 is advantageously atraumatic such that it will not cause damage to the interior of the vasculature during use. The separator 16 also assists in removing any clogs or flow restrictions that may develop within the lumen 36 due to the passage of thromboembolic material therethrough during aspiration.

Figure 11A:
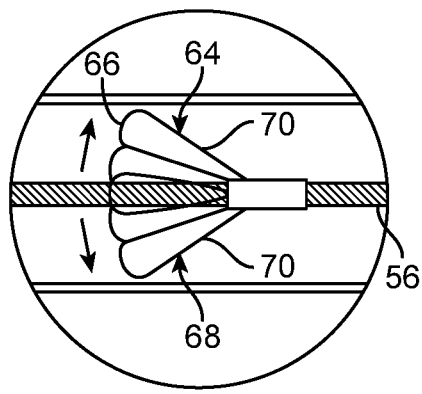
FIG. 11A is an enlarged view of the separator element forming part of the thromboembolic separator shown in FIGS. 9 and 10.

In one embodiment, as best shown in FIG. 11A, the separator element 64 may take the form of a basket that is generally conical in shape, with an opening 66 facing proximally along the elongated element 56. The separator basket 64 is dimensioned to assist in the thromboembolic fragmentation process, as well as to receive such thromboembolic fragments to aid in their removal. In one embodiment, the separator basket 64 is provided having a web 68 and one or more support members 70. The support members 70 are dimensioned to bias the web 68 into the generally open position shown and, if desired, to allow the web 68 to assume a generally closed position (not shown, but generally flush against the elongated element 56) as the separator 16 is passed through delivery and aspiration catheter-style pusher as described above, and/or the thromboembolism itself.

Figure 10:
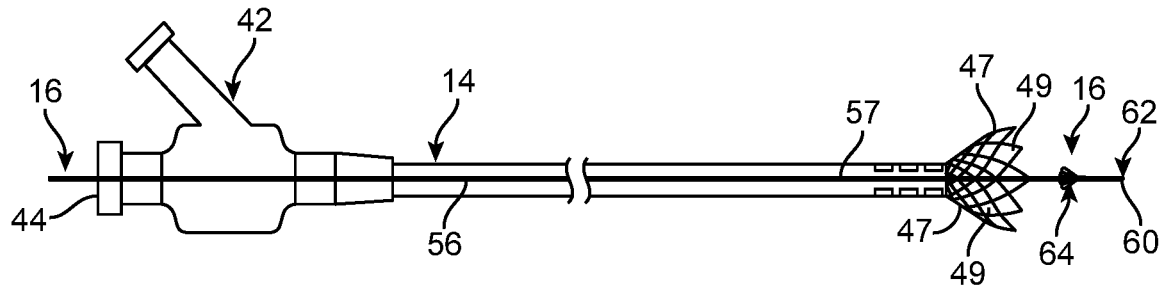

An alternative embodiment of a separator 16aa is shown in FIGS. 11B and 11C, in which like reference numerals are used to identify features similar to those shown in FIGS. 9, 10 and 11A. Separator 16a differs from separator 16 of FIGS. 9, 10 and 11A primarily in the features of the separator element 64a. Referring to FIG. 11B, separator element 64a is a conical member formed of a polymeric material such as polyurethane or Pebax® polyether block amides, to name a few. The separator element 64a is preferably a solid member, with a surface 65 facing in the proximal direction, and with the taper of the element oriented in a distal direction. Surface 65 may be contoured in a variety of ways. For example, surface 65 may be slightly concave as shown in FIG. 11B, substantially planar as shown in FIG. 11C, or slightly convex as shown in FIG. 11D.

The separator element 64a is positioned on the coiled distal section 57 of the elongate element 56. The pitch of a portion of the coiled section 57 may be decreased in certain regions of the coiled distal section 57. Opening the spacing in the coil in this manner can facilitate adhesion between the polymeric material of the separator element and the coil material during the molding process. The spacing between the separator element 64a and the distal end 60 of the elongate element 56 is preferably long enough to allow the distal-most portion of the elongate element sufficient flexibility to move atraumatically through the vasculature, but short enough to prevent folding of the distal-most portion during advancement of the elongate element 56. In an exemplary embodiment, the distal end of separator element 64a may be positioned approximately 3-9 mm from the distal end 60. It should be noted that the mandrel or core (not shown) within the coiled section 57 of the elongate element 56 might have a tapered diameter selected to enhance the flexibility of the coiled section.

A handle member 72 (FIG. 9) is provided at the proximal end 58 of the separator to provide a purchase point for a user to advance and/or manipulate the atraumatic tip element 62 and separator 64/64a. In one embodiment, the handle member 72 may be coupled to the elongated element 56 in any suitable fashion, including, but not limited to providing a generally rigid extension (not shown) disposed within the elongated element 56 for the purpose of coupling the two components together. This coupling may be augmented or strengthened through the use of any number of adhesives or fusing techniques.

The separator 16 may be provided in a variety of different permutations without departing from the scope of the present invention. For example, in addition to the "self deployable" embodiment described above, the separator basket 64 of FIG. 11A may be selectively deployed, such as by equipping the separator basket 64 with a mechanism to selectively bias or open the support members 70 from an initial position lying generally flush against the elongated element 56 to a generally radially expanded position (shown with arrows in FIG. 11A).

It will be appreciated that the guide and occlusion catheter 12, the delivery and aspiration catheter 14, the thromboembolic separator 16 and/or the thromboembolic receiver 46 may be provided with any number of features to facilitate the visualization of these elements during introduction and usage, including but not limited to having the distal regions equipped with radiopaque markers for improved radiographic imaging.

As discussed previously in connection with FIG. 1, the various components described herein may be provided as part of the system 10 for removing thromboembolic material. The thromboembolic removal system 10 may include a guide and occlusion catheter 12, a delivery and aspiration catheter 14, a thromboembolic separator 16/16a, a thromboembolic receiver (e.g. receiver 46 or 146), and an aspiration pump 18, as well as guidewires and/or other tools appropriate for the procedure. In one embodiment, multiple receivers 46/146 may be provided, allowing the surgeon to sequentially retrieve several thromboembolisms during the course of a procedure. For simplicity, each separate receiver may be provided with a separate delivery and aspiration catheter. The system 10 may additionally be provided with instructions for use setting forth any of the various methods of use described herein, or equivalents thereof.

System Use

Figure 12:
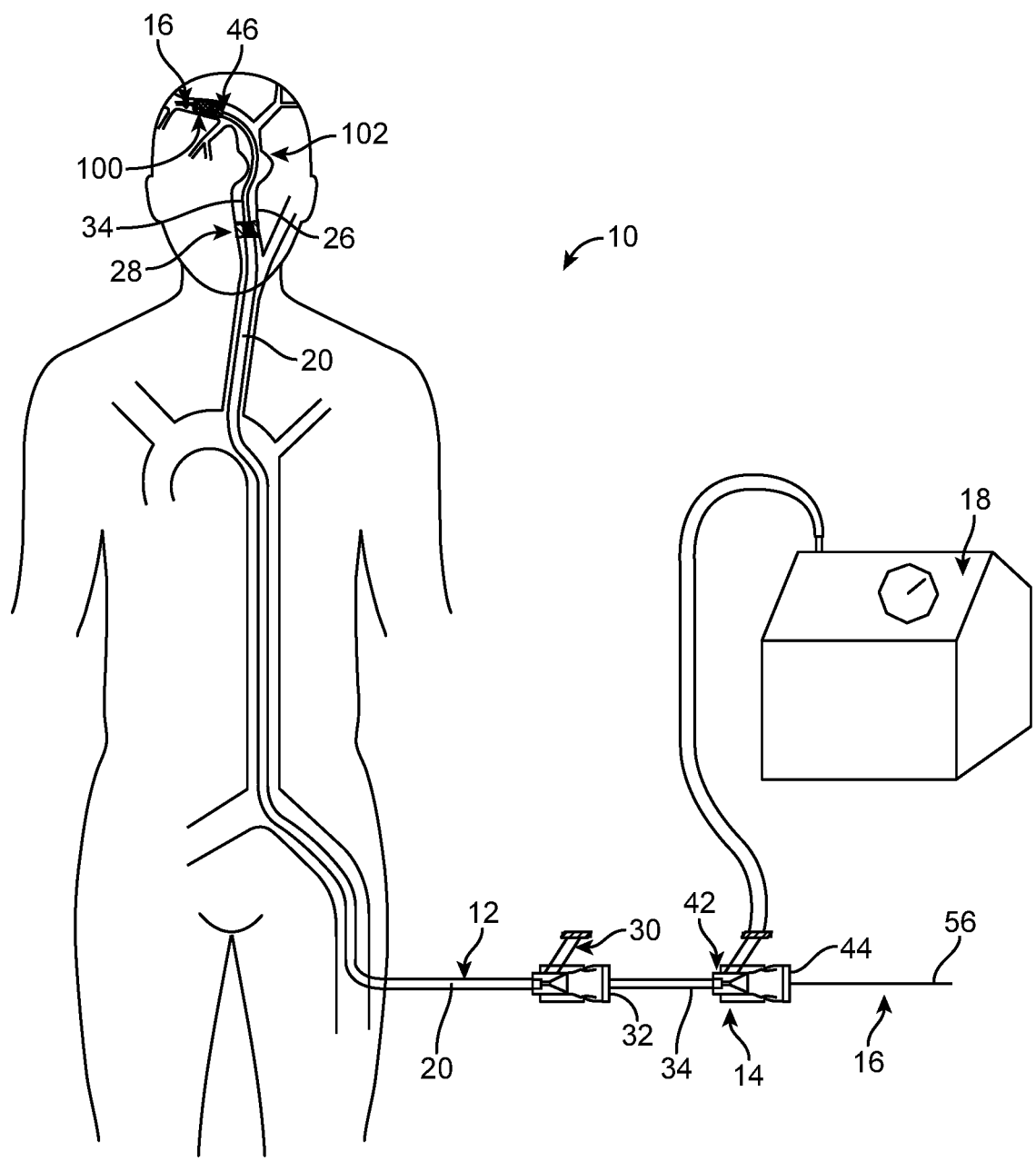
FIG. 12 is a partial sectional view of a patient illustrating the thromboembolic removal system of FIG. 1 in use within the arterial system.
Figure 13:
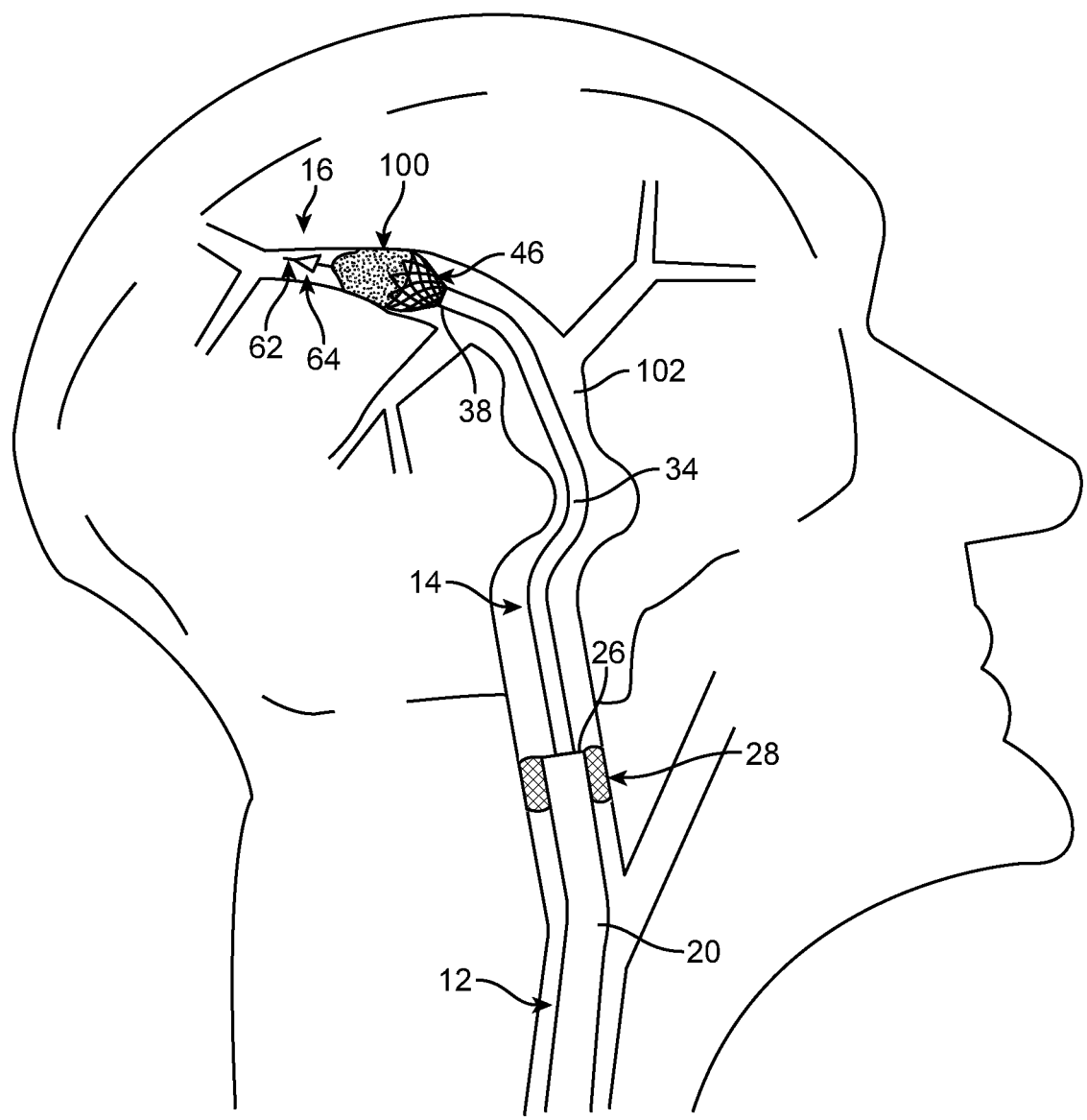
FIG. 13 is a partial sectional view of a patient illustrating the distal region of the thromboembolic removal system of FIG. 1 in use within a cerebral artery.
Figure 14:
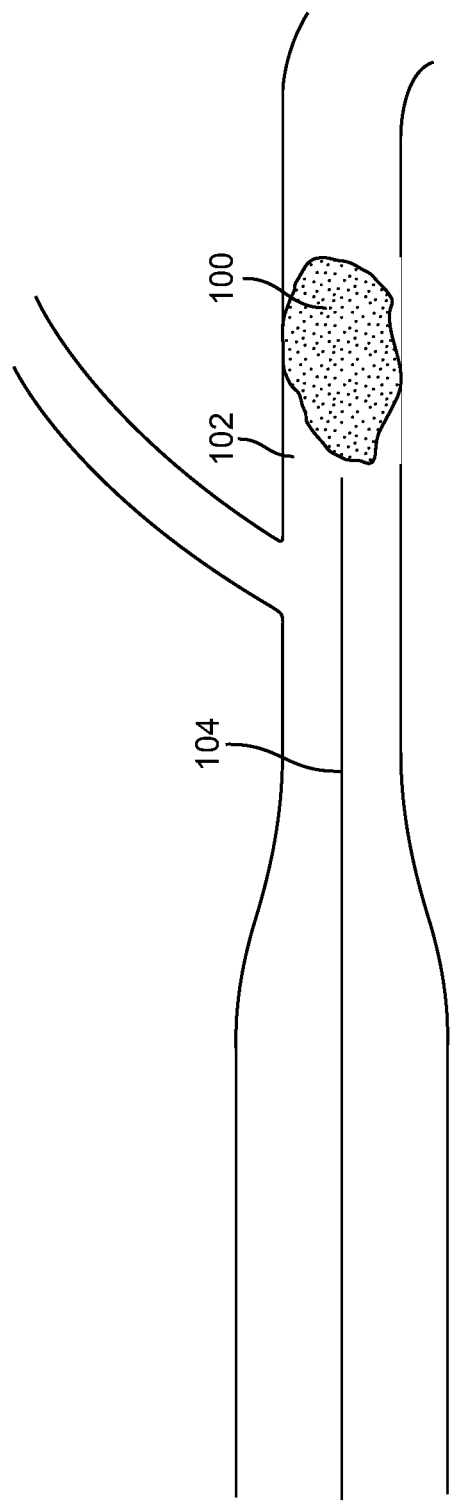
FIG. 14 is a partial section side view illustrating advancement of a guide wire to a thromboembolism.

Methods of using the thromboembolic removal system 10 will now be described with reference to FIGS. 12-28. As shown generally in FIGS. 12-13, in a first exemplary method the thromboembolic removal system 10 is introduced into the patient's vasculature, such as via the Seldinger technique. FIG. 14 illustrates the first step of this process, which involves advancing a guide wire 104 to a point proximal to a thromboembolism 100. The guide wire 104 may comprise any number of commercially available guide wires, the operation of which is well known in the art. However, in one method, the elongate member 56 (FIG. 11B) of the separator 16 functions as the guidewire 104.

Figure 15:
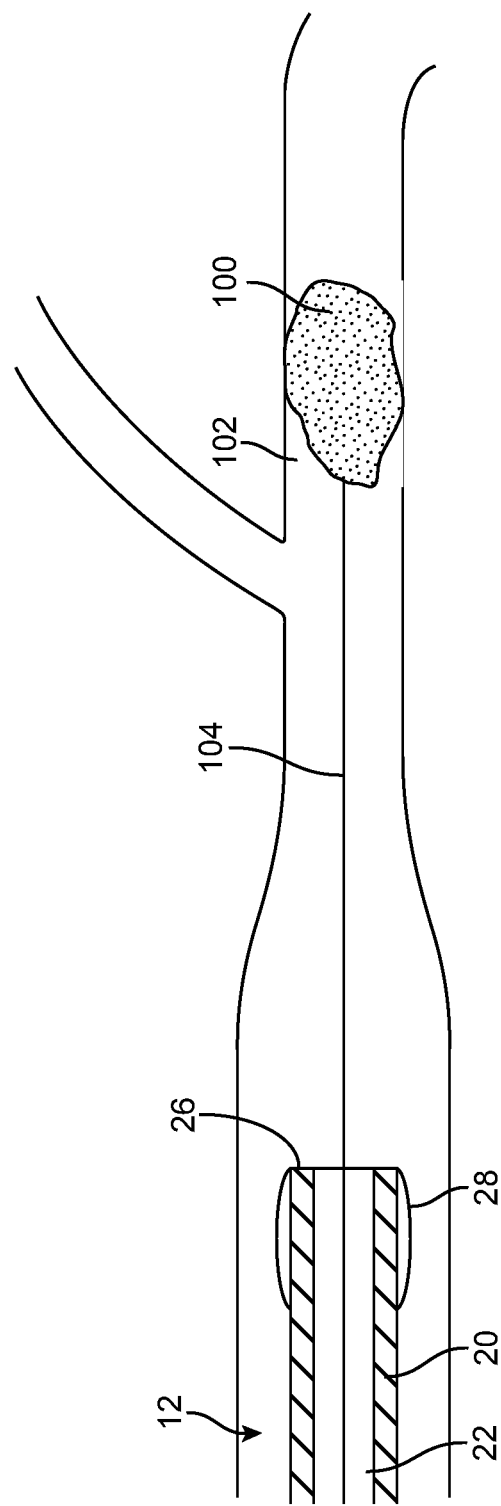
FIG. 15 is a partial section side view illustrating advancement of the guide and occlusion catheter, with the balloon in a deflated state.
Figure 16:
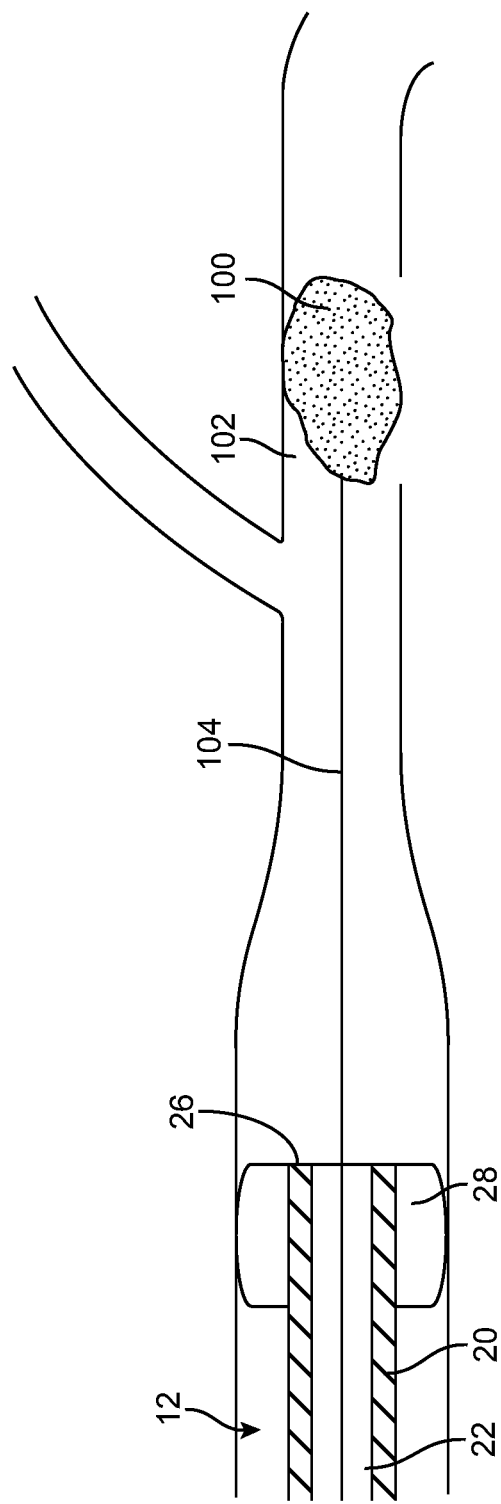
FIG. 16 is a partial section side view illustrating inflation of the balloon occlusion member to arrest the blood flow within the artery containing the thromboembolism.
Figure 17:
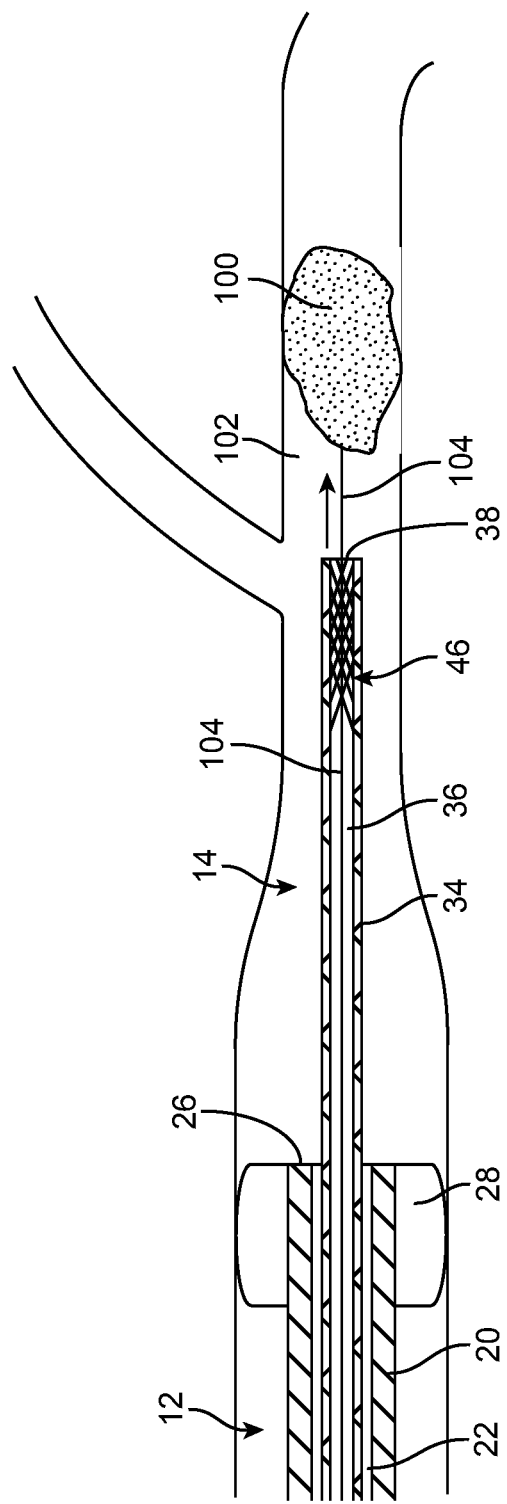
FIG. 17 is a partial section side view illustrating the step of advancing the delivery and aspiration catheter of FIGS. 1-3 to a point proximal to the thromboembolism according to a method for using the system of FIG. 1.

FIG. 15 illustrates a second step, which involves advancing the guide and occlusion catheter 12 over the guide wire 104 to a point proximal to the thromboembolism. The next step, shown in FIG. 16, preferably involves inflating the balloon occlusion member 28 so as to arrest the blood flow within the cerebral artery 102 containing the thromboembolism 100. As shown in FIG. 17, the delivery and aspiration catheter 14 is then advanced through the guide and occlusion catheter 12 such that the distal end 38 of the delivery and aspiration catheter 14 is positioned at a point proximal to the thromboembolism 100. This may be facilitated by advancing the delivery and aspiration catheter 14 over the guide wire (not shown but well known in the art) extending through the guide and occlusion catheter 12.

Figure 18:
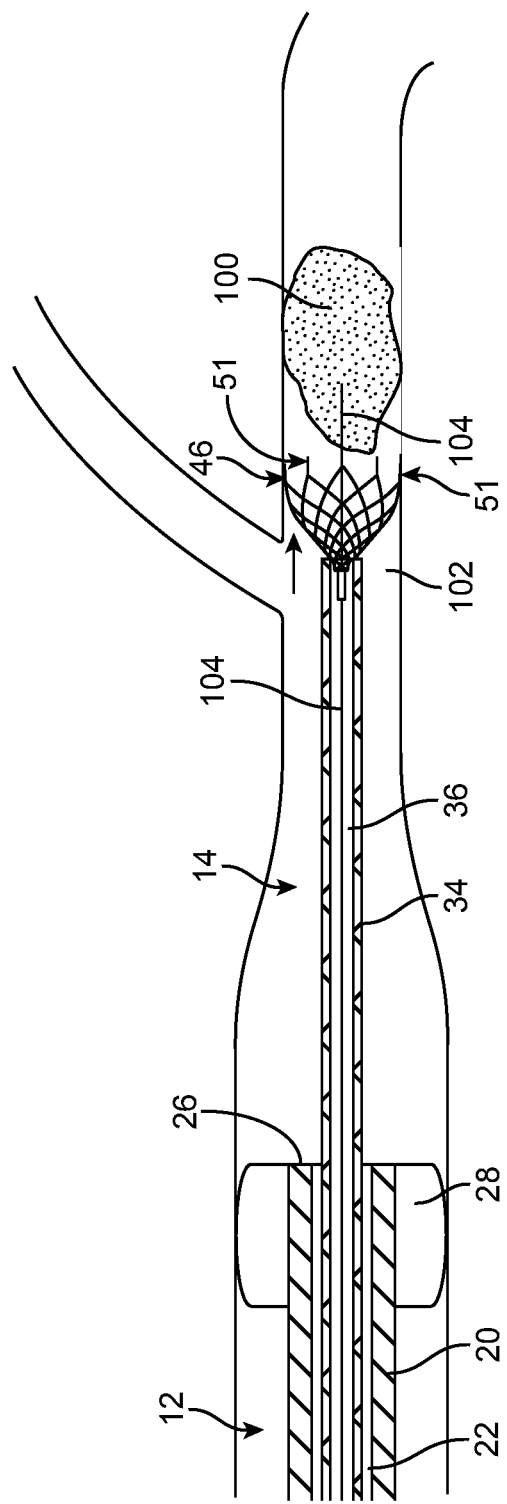
FIG. 18 is a partial section side view illustrating deployment of the thromboembolic receiver of FIGS. 1-3.
Figure 19:
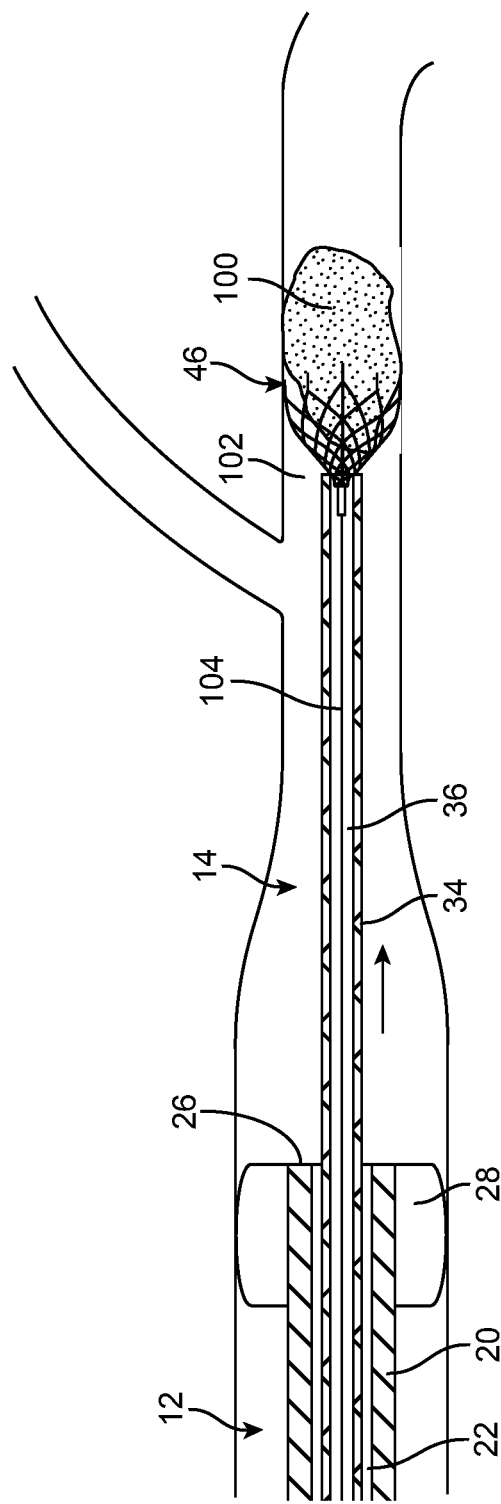
FIG. 19 is a partial section side view illustrating advancement of the delivery and aspiration catheter of FIGS. 1-3 distally such that the thromboembolic receiver of FIGS. 1-3 engages (fully or partially) the thromboembolism.
Figure 20:
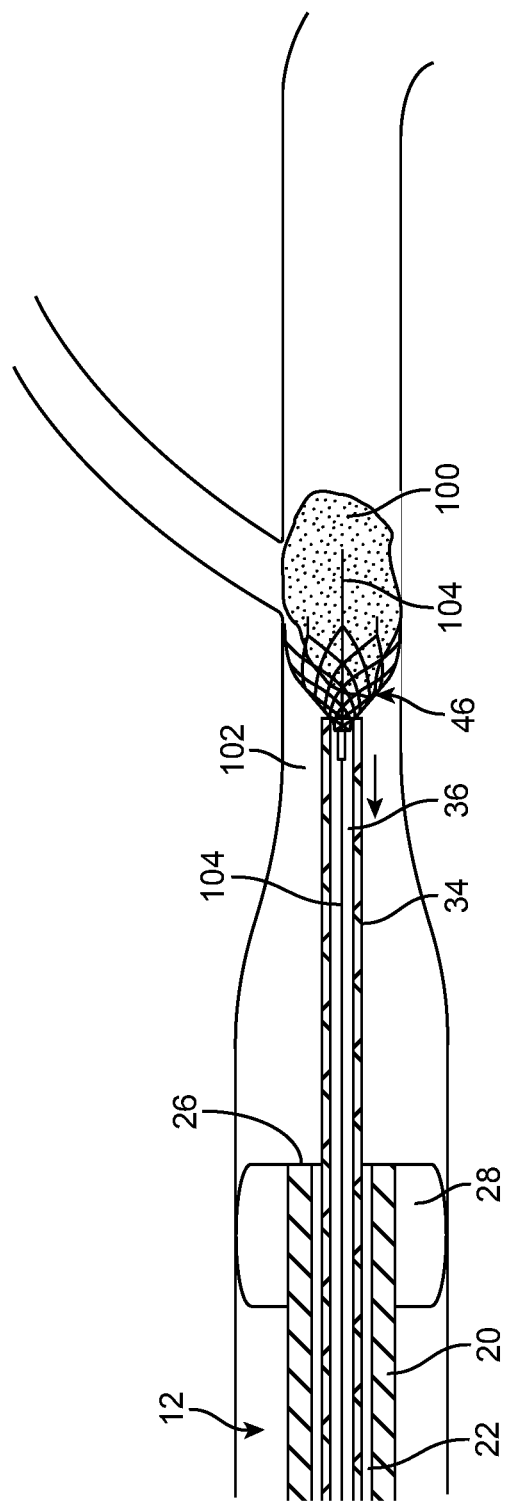
FIGS. 20 and 21 are partial section side views illustrating movement of the thromboembolic receiver of FIGS. 1-3 into the guide and occlusion catheter so as to remove the thromboembolism.
Figure 21:
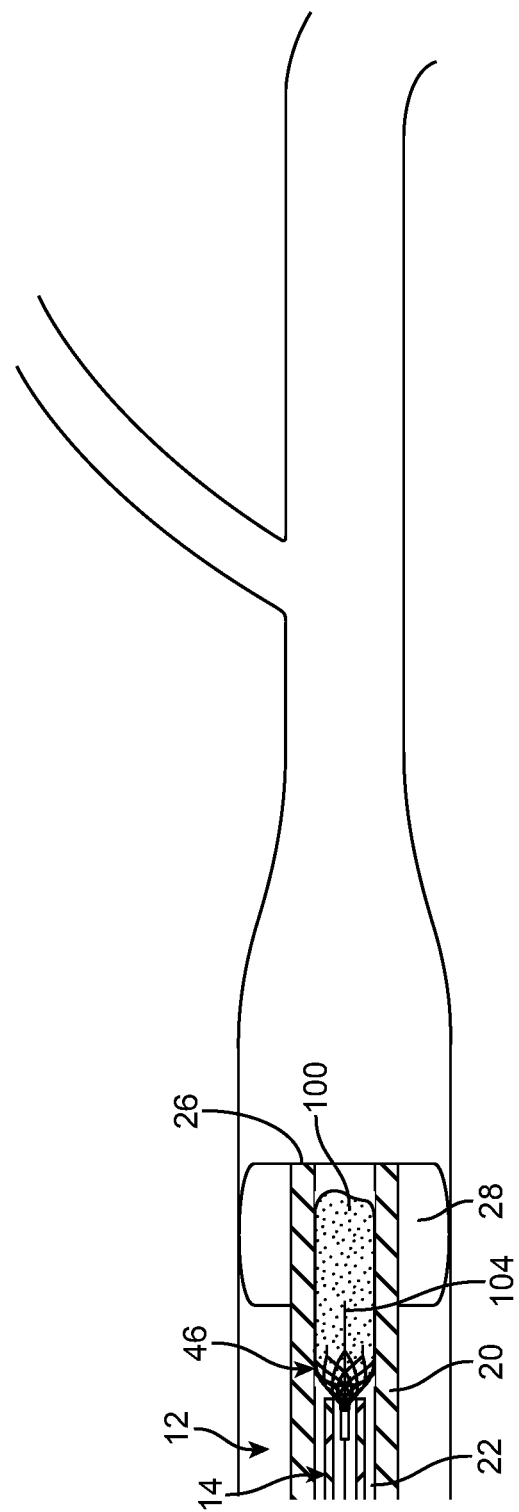

At this point, as shown in FIG. 18, the thromboembolic receiver 46 is deployed from the distal end 38 of the delivery and aspiration catheter 14. In one embodiment, the balloon occlusion 28 may be inflated at this point (as opposed to inflating it before the delivery and aspiration catheter 14 is advanced, as shown in FIG. 16). The delivery and aspiration catheter 14 is then advanced distally—as shown in FIG. 19—such that the thromboembolic receiver 46 engages and/or envelops (partially or fully) the thromboembolism 100. At this point, as shown in FIGS. 20 and 21, the delivery and aspiration catheter 14 may be withdrawn into the guide and occlusion catheter 12 to remove the thromboembolism 12 from the patient.

To augment the ability to remove the thromboembolism 100, or in the instance the thromboembolic receiver 46 does not initially engage the thromboembolism 100, the aspiration pump 18 may be activated to establish negative pressure within the delivery and aspiration catheter 14. In this fashion, negative pressure will be created within the cerebral artery 102 and exerted upon the thromboembolism 100. As noted above, the separator 16 (or the separator 16a of FIGS. 11B-D) may be employed during this process (e.g. advancing and retracting it within the lumen 36 of the delivery and aspiration catheter 14) to remove any clogs or flow restrictions due to the passage of thromboembolic material through the lumen 36. The negative pressure will serve to draw the thromboembolism 10 into (partially or fully) the thromboembolic receiver 46. The delivery and aspiration catheter 14 may then be withdrawn into the guide and occlusion catheter 12 to remove the thromboembolism 100 from the patient.

Figure 22:
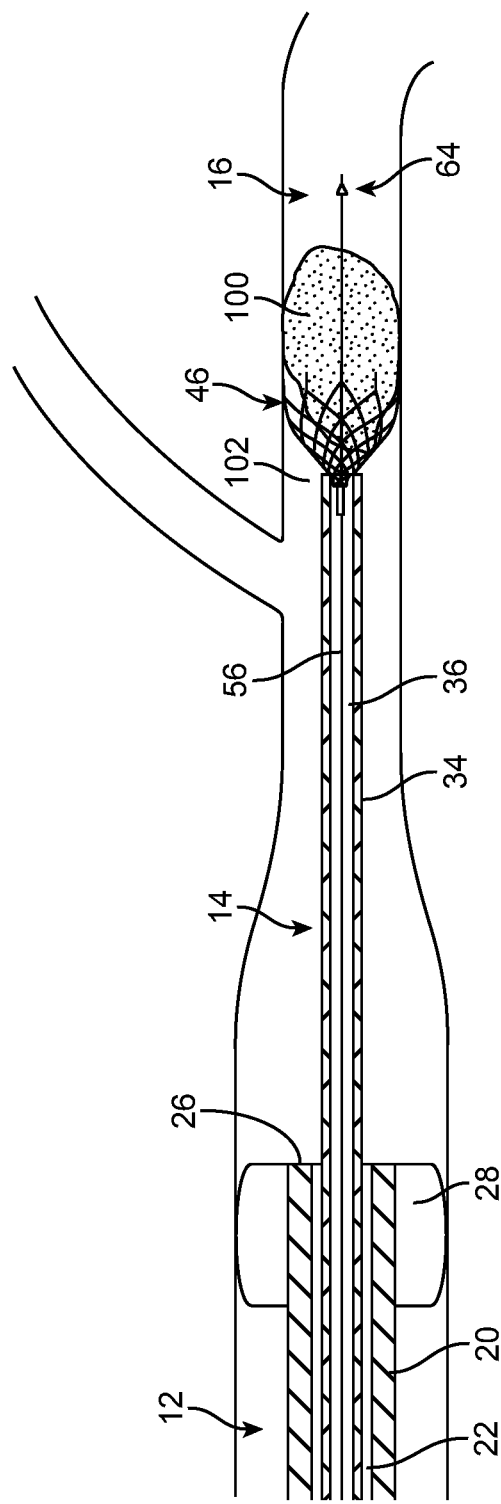
FIG. 22 is a partial section side view illustrating use of the thromboembolic separator of FIGS. 1 and 9-11C to engage the distal end of the thromboembolism.

To further augment the ability to remove the thromboembolism 100, or in the instance the aspiration pump 18 does not adequately draw all or most of the thromboembolism into the receiver 46, the thromboembolic separator 16/16a may be advanced into contact with a portion of the thromboembolism, or completely through the thromboembolism 100 as shown in FIG. 22, and employed to bias or engage the distal end of the thromboembolism 100. This will increase the surface area of engagement with the thromboembolism 100, which will advantageously allow it to be withdrawn into the guide and occlusion catheter 12 such as by withdrawing the separator 16/16a and delivery and aspiration catheter 14 simultaneously into the guide and occlusion catheter 12.

Figure 23:
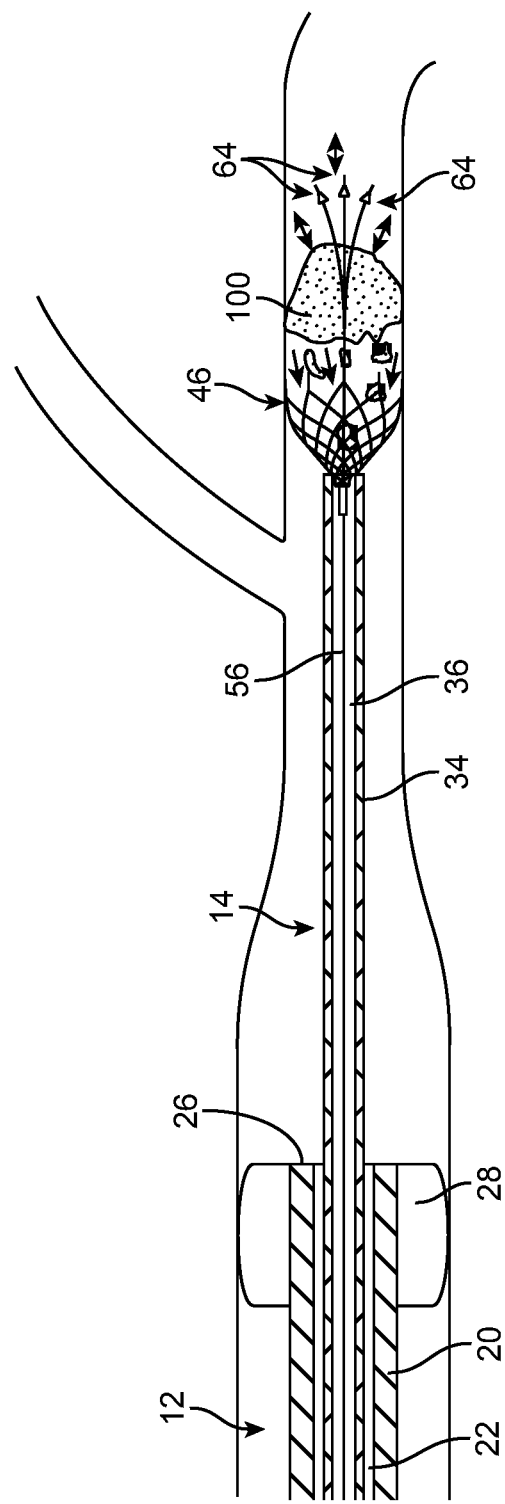
FIG. 23 is a partial section side view illustrating use of the thromboembolic separator of FIGS. 1 and 9-11C to fragmentize and/or soften the thromboembolism and/or aid aspiration.

As shown in FIG. 23, the separator 16/16a may also be selectively advanced and retracted through the thromboembolism 100 (or that remaining outside the receiver 46). This will serve to break up or otherwise soften the thromboembolism 100. Advancing and retracting the separator 16/16a also serves to remove any clogs or flow restrictions within the lumen of the delivery and aspiration catheter 14 during the aspiration due to the passage of thromboembolic material through the lumen 36 of the delivery and aspiration catheter 14. In either event, the aspiration pump 18 will draw or bias the thromboembolic fragments 106 or the softened thromboembolism 100 into the thromboembolic receiver 46 and/or into catheter 14. The delivery and aspiration catheter 14 may then be withdrawn such that the thromboembolic receiver 46 is drawn into the guide and occlusion catheter 12 to remove the thromboembolism 100 from the patient.

Selective advancement of the separator element 64 through the thromboembolism and retraction of the separator element into the delivery and aspiration catheter 14, preferably in combination with aspiration, can additionally be used to carry small "bites" of the thromboembolic material, displacing some material and thus forming a channel in the material as it moves distally. Once the separator element is positioned further into, or distally of, the thromboembolism, some of the displaced material may flow back into this channel. Subsequent retraction of the separator element 64 through the material (e.g. through the re-filled channel) will then draw some of the material into the catheter 14. To facilitate this procedure, the separator element 64 and the catheter 14 are preferably provided with fairly tight tolerances between the diameter of the catheter lumen 36 and the greatest diameter of the separator element 64. For example, in one exemplary embodiment, the outer diameter of separator element 64 and the diameter of lumen 36 may differ by approximately 0.003-0.008 inches.

An alternative method will next be described in which the receiver and disrupter are preferably used independently of one another, although combined use such as that described in connection with the first exemplary method might also be used. This method will be described as performed using the thromboembolic receiver 146 and the separator 16a, however it should be appreciated that other embodiments of these components may alternatively be used in the disclosed method.

According to the alternative method, an initial determination is made concerning whether use of receiver 146 or separator 16a will first be employed. This determination may be made at random, although in a preferred method the surgeon selects the appropriate tool based on a determination of the likely nature of the thromboembolic material that is to be removed. In particular, the surgeon will assess the patient to determine whether the material is likely to be hard or soft/gelatinous. This assessment might include an evaluation of one or more factors such as the response of the tip of the guidewire or separator when it is brought in contact with thromboembolism, the location of the thromboembolic material, patient symptoms, and/or the manner in which the stroke caused by the thromboembolism is manifesting itself.

As discussed in connection with the first exemplary method, the guide and occlusion catheter 12 is introduced into the patient's vasculature, and the occlusion balloon 28 is inflated to arrest the flow of blood within the vessel (see, for example, FIGS. 14-16).

The delivery and aspiration catheter 14 is passed through the guide and occlusion catheter 12 and positioned with its distal end at a location proximal to the thromboembolism 100. If the surgeon elects to use the separator 16a prior to using the receiver 146, or if the assessment results in a determination that the thromboembolic material is likely to be somewhat soft or gelatinous, the aspiration pump 18 is activated to establish negative pressure within the delivery and aspiration catheter 14, and thus to exert negative pressure exerted upon the thromboembolism 100 to draw embolic material into the catheter 14.

Figure 24:
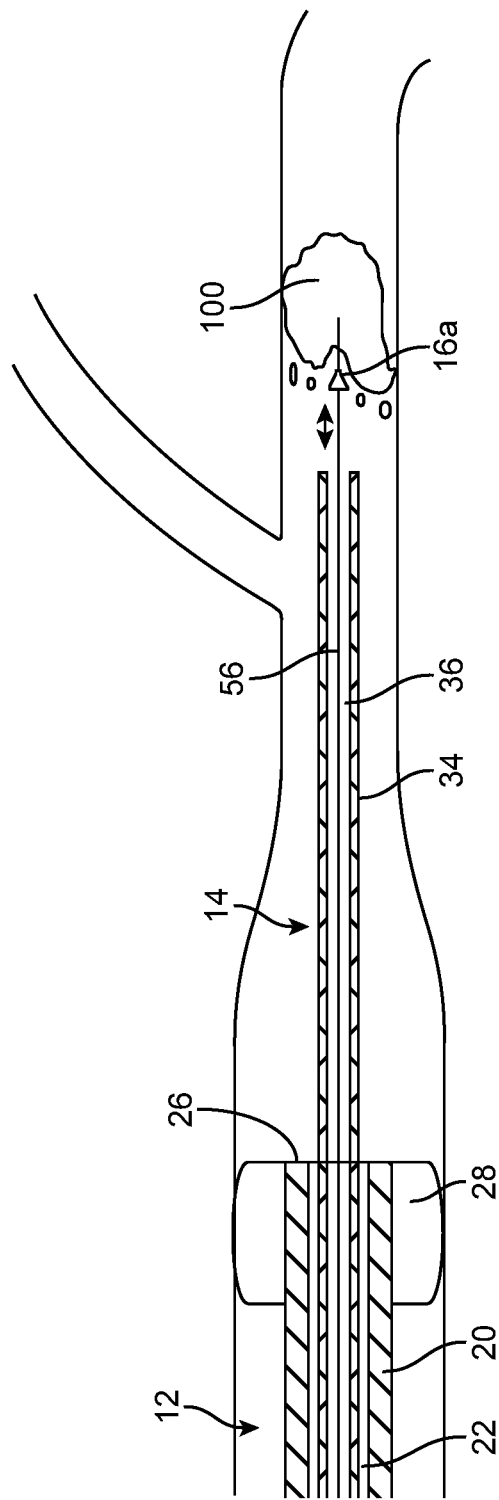
FIG. 24 is a partial section view illustrating independent use of the thromboembolic separator of FIGS. 1 and 9-11C to fragmentize and/or soften the thromboembolism and/or aid aspiration.
Figure 25:
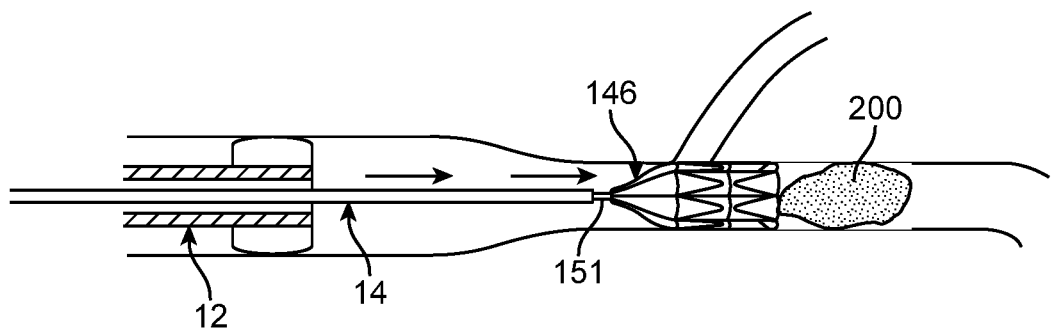
FIGS. 25 and 26 are partial section side views illustrating advancement of the thromboembolic receiver of FIGS. 4-6 distally such that it envelopes the thromboembolism.
Figure 26:
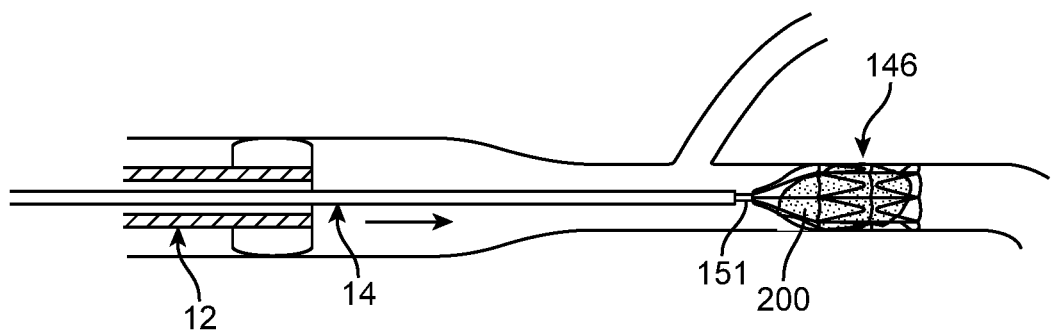
Figure 27:
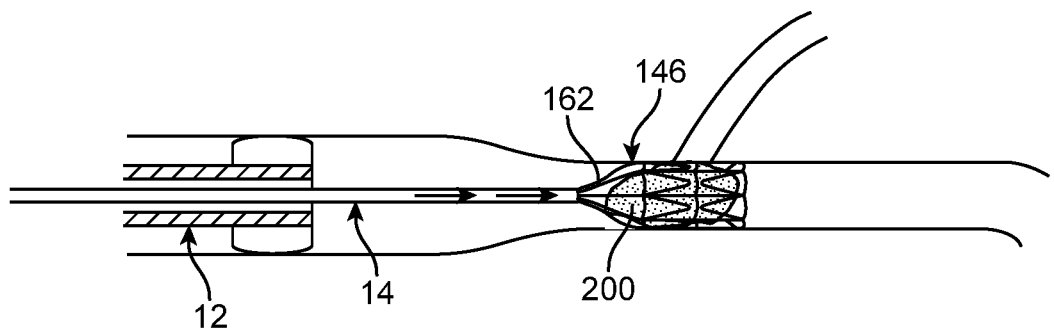
FIGS. 27 and 28 are a partial section side views illustrating withdrawal of the thromboembolic receiver of FIGS. 4-6 and the delivery and aspiration catheter into the guide and occlusion catheter so as to remove the thromboembolism.
Figure 28:
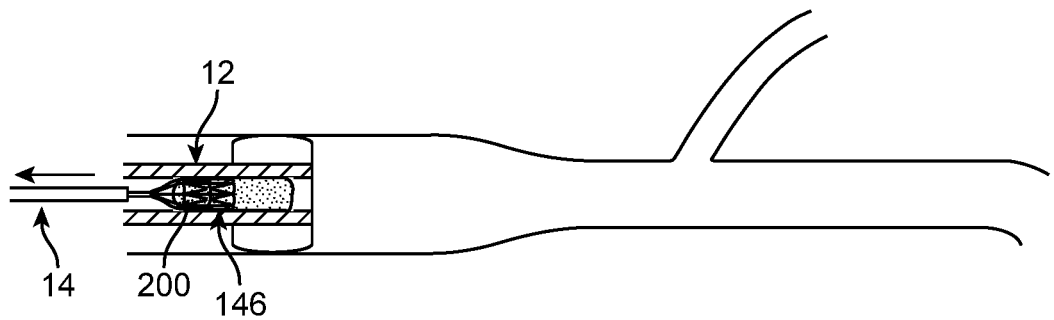

The separator 16a is deployed from the distal end of the delivery and aspiration catheter 14 and moved into contact with the thromboembolic material 100 as shown in FIG. 24. The separator may be advanced and retracted multiple times if desired. When advanced and retracted as shown, the separator can facilitate aspiration of the thromboembolic material into the catheter 14 in one of a variety of ways. First, movement of the separator into contact with the thromboembolism can loosen, separate, or soften pieces of thromboembolic material, such that pieces of the thromboembolism can be aspirated into the catheter. Second, advancing and retracting the separator 16a serves to remove any clogs or flow restrictions within the lumen 36 of the delivery and aspiration catheter 14 that might be caused by the passage of thromboembolic material through the lumen 36. Additionally, during retraction of the disrupter 16a, its proximal surface 35 may push or plunge loosened material towards and/or into the distal end of the catheter 14 for subsequent aspiration out of the body.

If use of the disrupter 16a as just described reveals that the vessel includes a hard mass of thromboembolic material incapable of aspiration without further intervention, the disrupter 16a is preferably withdrawn from the catheter 14 and a thromboembolic receiver 146 is passed through the delivery and aspiration catheter 14 and deployed within the blood vessel. If the system is provided with multiple sizes of receivers, the surgeon will select a receiver having an appropriate size for the blood vessel being treated.

Referring to FIGS. 25-28, once the receiver 146 is deployed, it expands into contact with the surrounding walls of the vessel. As the receiver 146 is advanced towards the body thromboembolic material 200, the walls of the receiver 146 slip around the body 200 to engage and/or envelop (partially or fully) the thromboembolism. The engaging elements 170 engage the thromboembolism 200, thereby retaining it within the receiver. If desired, the delivery and aspiration catheter 14 may be advanced slightly in a distal direction as indicated by arrows in FIG. 27, so as to "cinch" the strut members 162 towards one another, thus causing the receiver 146 to collapse slightly in a radially inward direction. Additionally, the aspiration pump 18 (FIG. 1) may be activated to facilitate retention of the thromboembolism 200 within the receiver. The delivery and aspiration catheter 14, the receiver 146 and the thromboembolism 100 are withdrawn into the guide and occlusion catheter 12 and are withdrawn from the body. If additional thromboembolic material should remain in the blood vessel, a new delivery and aspiration catheter 14 may be passed into the blood vessel, and a new receiver may be deployed through the catheter 14 for retrieving the additional body of thromboembolic material.

Naturally, the surgeon may elect to initially deploy the receiver rather than the separator, such as if the initial assessment results in a determination that the thromboembolic material is likely to be hard. The method is then carried out utilizing the receiver 146 as described in the preceding paragraph. If it is later determined that residual thromboembolic material (e.g. soft or gelatinous material) is present in the vessel, the receiver 146 is preferably removed from the body, and the separator 16a is passed through the delivery and aspiration catheter 14. The aspiration pump 18 is activated and the separator 16a is manipulated to facilitate aspiration of the soft material in the manner described above.

Figure 29:
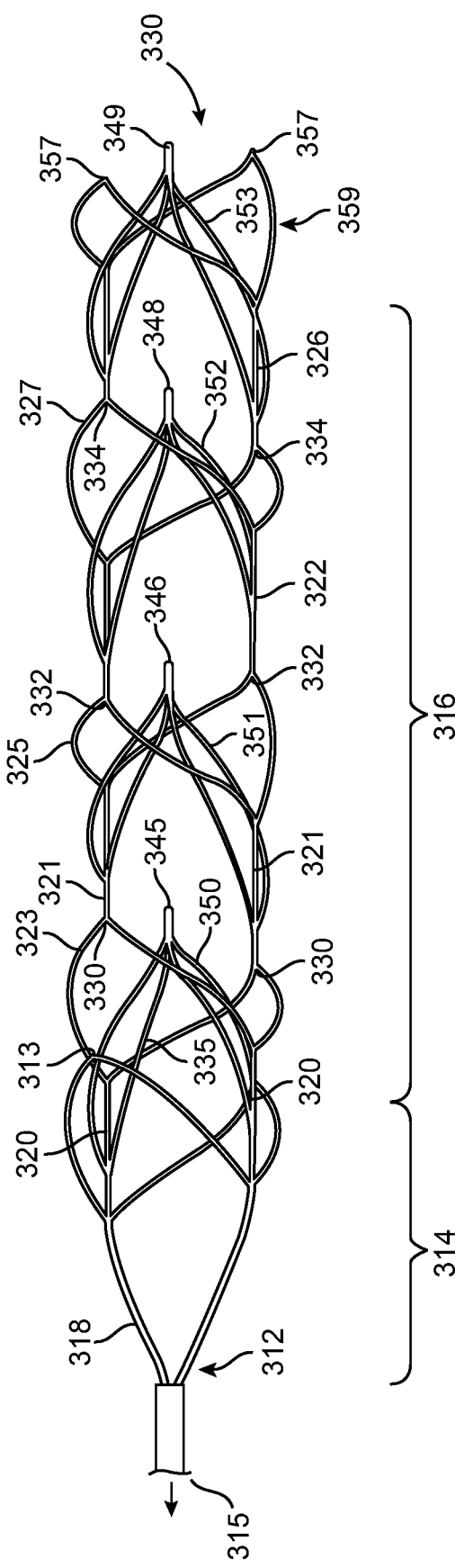
FIG. 29 is a perspective view of yet another alternate thromboembolic separator, which combines some of the features of a receiver and a separator in order to function as an improved separator equipped with a series of engagement cages, where the engagement cages are framed by uprights and apexes, and each engagement cage is defined by a pair of rib apexes that is adjoined to an adjacent pair of rib apexes.
Figure 30:
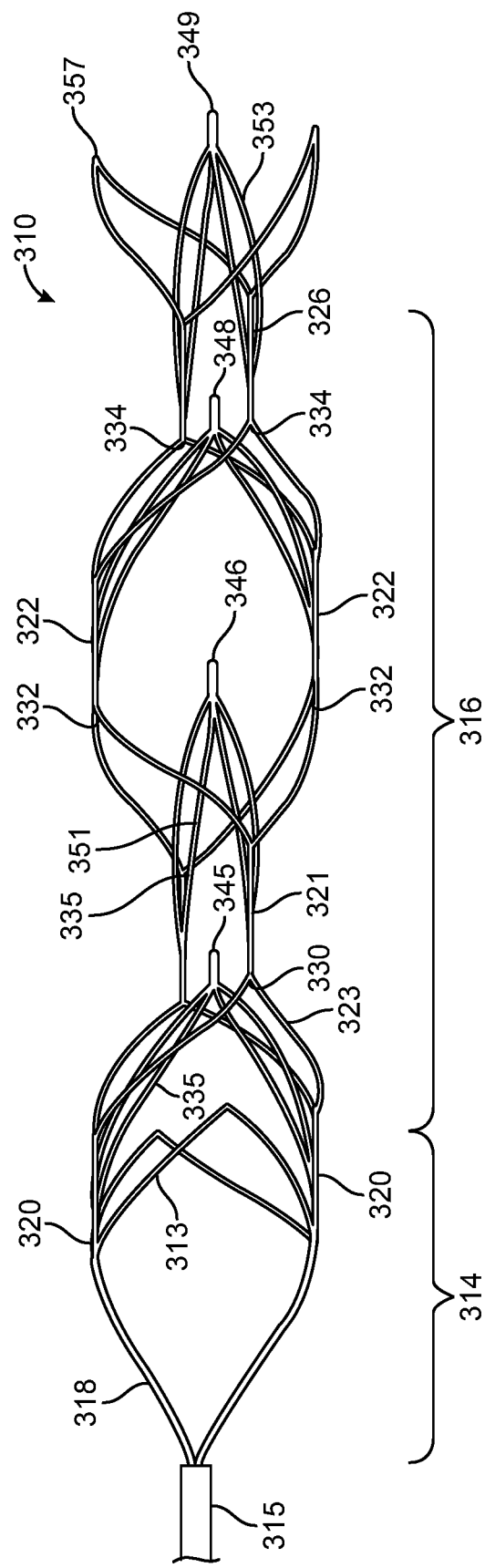
FIG. 30 is an alternate perspective view of the thromboembolic separator of FIG. 29. The thromboembolic separator of FIG. 29 is rotated slightly to reveal the perspective view of FIG. 30.

Referring now to FIGS. 29 and 30, an alternate embodiment of a thromboembolic separator 310 is shown. The thromboembolic separator of FIGS. 29 and 30 combines many of the features of the receivers and separators discussed above, in order to perform as an improved separator. FIG. 29 is a perspective view of thromboembolic separator 310. FIG. 30 is also a perspective view of thromboembolic separator 310, but is rotated slightly from the view of FIG. 29 in order to reveal characteristics that are not visible in FIG. 29. In turn, FIG. 29 can be consulted for an illustration of features that are slightly obstructed in the view of FIG. 30. Thromboembolic separator 310 may be constructed from any number of materials or compositions having suitable biocompatibility and strength characteristics, and may be dimensioned in any number of suitable sizes and lengths depending upon the location of the thromboembolism, variances in patient anatomy, and the size and shape of the thromboembolism. In the embodiment illustrated in FIGS. 29 and 30, the outer diameter of separator 310 in its deployed (radially expanded) configuration may range between 4.6 mm and 5.4 mm to be used in vessels ranging from 3.0 mm and larger; however other device diameters may be suitable according to the invention. The length of separator 310 when deployed may vary between 12 mm and 20 mm, but preferably is longer than the length of the thromboembolism, and in this instance is approximately 17 mm.

Separator 310 is constructed from a nickel-titanium alloy (Nitinol®) with "shape memory" or superelastic characteristics. Accordingly, the thromboembolic separator 310 is capable of being retained in a constrained form or shape prior to deployment. The separator may be formed by laser cutting features into a length of Nitinol tubing, then chemically etching and shape-setting the material, and then attaching cut features to one another to construct a finished device. For example, a tube of 3.5 mm outer diameter and 0.0055 inch wall thickness may be cut in a predetermined pattern. Examples of suitable patterns are illustrated as flat patterns in FIG. 31, FIG. 34 and FIG. 37 (as though the tube were cut along a longitudinal axis and laid flat). Other patterns may also be suitable. Strut widths that define the elements of separator 310 may vary between 0.0011 inch and 0.00165 inch. Struts may have a broadened region and one or more tapered regions. After the features are cut into the length of tubing, additional steps (which are described in greater detail below) are performed upon the features of the cut tube in order to manufacture the finished separator 310.

The elements of thromboembolic separators according to the invention and illustrated in FIGS. 29-37 are defined by strut members cut into the tubing, some of which undergo additional processing in the manufacture of the finished device. A strut member as used herein is a generic term for a band-like, wire-like, or other elongate element cut out of the tubing in the early steps of manufacture of a separator according to the invention. Because a separator according to the invention typically has numerous strut members having varied configurations, other terms are used in the following description to distinguish among strut members and in order to avoid confusion. Nonetheless, a particular strut member will be longitudinal or transverse, curved, undulating, straight deflected inwardly to occupy a lumen of the tubular separator, or the like. The length and width of a strut member may differ from that of another strut member and may perform a different function in the device. An individual strut member may have either a uniform or a varied width along its length.

Some strut members are configured to define "uprights" or "standards". The terms upright or standard are used interchangeably to describe a strut member that extends generally longitudinally (in a direction parallel to a central axis of the tube) along the length of the device. An upright or standard will typically confer axial or columnar strength upon the device. In addition, uprights are typically more or less parallel to one another throughout the length of the device. A first set of uprights at the base of the device may be referred to as "legs". An upright or standard may be the same width as or wider than other strut members that define the device's structure. An embodiment according to the invention may have any number of uprights, but those described in detail herein typically have between two and four uprights or standards.

While uprights are more or less parallel to one another, some strut members extend from the uprights or standards at an angle to the upright. The angle at which a particular strut member is oriented to a particular upright may vary widely, and the term angle should be understood to mean any angle within the full spectrum greater than 0 degrees and less than 180 degrees, but will most often be between 15 degrees and 75 degrees. The strut members that extend from an upright at an angle to the upright meet other strut members attached to an opposite upright and also extending at an angle to the opposite upright. The term "apex" is used herein to refer to two strut members that meet at their distal end to form a peak or "apex". An apex may be pointed or rounded, may be attached to an upright, to another apex (so that in effect four struts meet at a common apex), or may be free. An apex may be slightly "cupped" in a deployed device. An apex may be disposed along a "wall" of a separator or, alternatively, may be disposed or deflected to lie within a central "lumen" of the separator. Further, an apex may include an additional extension therefrom.

An apex that is left free is referred to as an apex, but with an added indication of the relative location of the apex. For example, a proximal apex is located at the proximal end of the device, and a distal apex is located at the distal end of the device. A body apex is located along the body of the device, and may be numbered consecutively as first body apex, second body apex, and so on, from the proximal end of the device to the distal end of the device. An apex that is attached at its distal end to an upright may be referred to as a "fork" at its point of attachment to the upright. And an apex that is formed where the distal end of an upright divides may be described as "Y-like". An apex that may be coupled to another apex in the central lumen of the device is referred to as a "peak", whether the apex is coupled or remains unattached in the finished device. An attached pair of peaks, typically disposed within the central lumen of the device, is referred to as a "cage".

Some of the strut members that extend from the uprights at an angle to the uprights are given the term "rib" and some are given the term "arm", depending upon what structure the strut member is attached to. A "rib" is typically a strut member that extends from an upright at an angle to the upright until it meets another rib coming from an opposing upright to define a "peak". A peak may also have a "rib extension" extending therefrom. A peak and its respective rib extension may define a wish-bone like configuration. A peak may be attached to another peak or may remain unattached in a finished device. Where a peak is coupled to a second peak, the paired rib peaks are referred to as a "cage". Ribs, peaks, and rib extensions forming a cage are typically biased into the central lumen of the device when they are coupled with a second pair of ribs, peaks and extensions.

An "arm" is also a strut that extends from an upright at an angle to the upright. Arms extend generally in a "Y-like configuration" in a distal direction from an upright. Distal to the point where arms divide in a Y-like fashion, two arms meet again at a subsequent upright. The term "fork" may be used to describe the point at which two arms meet at a distal upright to define an apex. While all of the foregoing terms refer to struts and apexes, it is hoped that the additional terms enable a clearer distinction among struts and apexes and a clearer description of a device according to the invention.

After material is removed from a Nitinol tube according to a predetermined pattern, and following the final steps to construct separator 310, the structure of separator 310 is a generally skeletal device bearing "internal" elements. The body abstracted from the tube has large voids in its "walls" and loosely defines a central axis 330 therethrough. The abstract tube has an outer circumference disposed about the central axis. The series of internal elements is disposed about central axis 330. These internal elements are referred to as engagement cages 350, 351, 352 and 353. Separator 310 (FIGS. 29 and 30) includes four such engagement cages 350, 351, 352 and 353, but may according to the invention include a greater or lesser number. Engagement cages 350, 351, 352 and 353, along with other elements of the device, engage embolic material in a vessel of a subject during use of separator 310, in order that the embolic material may be removed and vessel patency restored.

Engagement cages 350, 351, 352 and 353 are framed first by uprights (or standards) 320, 321, 322 and 326 respectively. Engagement cage 350 is also framed by proximal apexes 313, and by two pairs of arms 323. Proximal apexes 313 may cup slightly in the expanded device. Each pair of arms 323 meets to form forks 330 at subsequent uprights 321. Engagement cage 351 is also framed by two pairs of arms 325. Each pair of arms 325 meets to form forks 332 at subsequent uprights 322. Similarly, engagement cage 352 is also framed by two pairs of arms 327, which meet to define forks 334 at subsequent uprights 326. And engagement cage 353 is framed by distal apexes 357. Similar to proximal apexes 313, distal apexes 357 may cup slightly in an expanded device.

In FIGS. 29 and 30, separator 310 is shown mounted to pusher 315, which is proportioned to extend through the lumen of a delivery and aspiration catheter such as the PX400 catheter or other suitable catheters available from Penumbra, Inc. in Alameda, Calif. Other straight lumen catheters having an inner diameter of between 0.025-0.032 inch may be suitable. A suitable pusher catheter may be constructed from Pebax HS tubing or comparable material, available from Zeus Medical of Orangeburg, S.C., though other materials and alternative dimensions may be suitable according to the invention. A separator according to the invention may in the alternative be mounted to a delivery wire, depending upon the dimensions and requirements of the delivery catheter used to deliver the separator to the treatment site. A delivery wire may be of 0.014 inch distal diameter and 0.020 inch proximal diameter stainless steel, Nitinol or other metal, or other suitable dimensions and materials. If mounted upon a delivery wire, separator 310 may be mounted approximately 5 cm from the distal end of the wire, but other configurations are possible. Separator 310 may advantageously be mounted eccentrically to the pusher or delivery wire. Thromboembolic separator 310 is mounted to the distal end of pusher 315 via legs 318.

Figure 31:
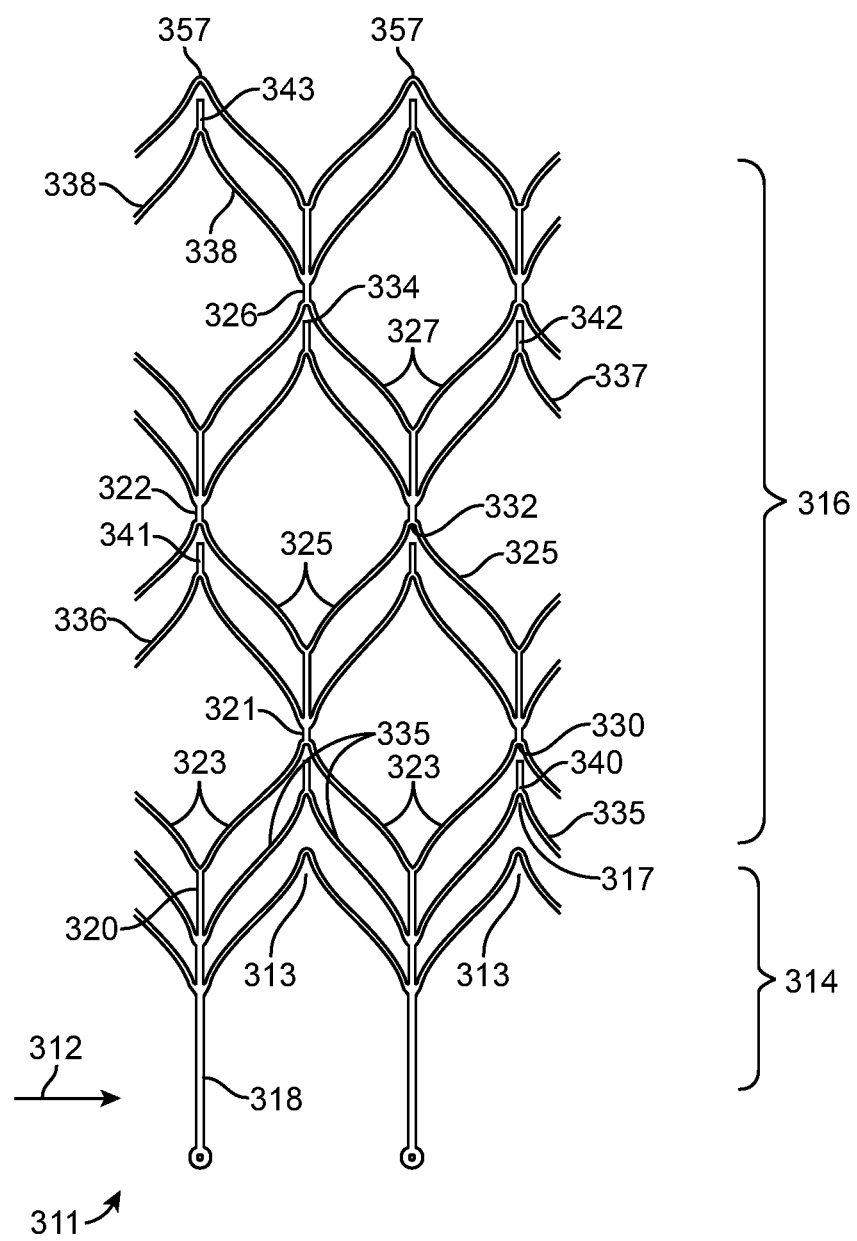
FIG. 31 is a plan (rolled out) view of the cut pattern of the thromboembolic separator of FIGS. 29 and 30. Although the separator is preferably a generally tubular structure.

The separator 310 illustrated in FIGS. 29 and 30 is finished, but many of its features may be more readily understood by referring to FIG. 31. FIG. 31 illustrates flat (rolled out) pattern 311. Beginning at its proximal end 312, legs 318 extend distally to form a first set of uprights 320. Proximal apexes 313 are attached between adjacent uprights 320. Base end 314 of separator 310 is thereby defined by legs 318, uprights 320, and proximal apexes 313. Proceeding distally from proximal apexes 313, and ignoring ribs 335 (and engagement cages 350-353 of the deployed device) for now, the distal end of each upright 320 divides in a Y-like fashion to form a first set of arms 323. Each arm 323 extends at an angle to uprights 320, or generally diagonally to meet an adjacent arm 323 at fork 330 as each arm 323 joins a subsequent set of uprights 321 extending therefrom. This pattern, which can be most easily seen in FIG. 31, repeats until the distal end 359 of separator 310. The body 316 of separator 310 is thus defined primarily by successive sets of uprights 320, 321, 322 and 326, successive sets of arms 323, 325 and 327, and forks 330, 332, and 334, where the number of the sets can vary according to the invention. Uprights 320, 321, 322 and 326, arms 323, 325 and 327, and forks 330, 332 and 334 skeletally frame a series of engagement cages, which will be described in detail below. Each set of uprights is oriented around the circumference of separator 31 at roughly 90° to its adjacent set of uprights, as most easily seen in FIG. 30.

The distal end 359 of separator 320 is defined by distal apexes 357, which in the deployed separator 310 cup slightly and are oriented at approximately 90° about the central axis 330, or around the device's circumference, to proximal apexes 313. Distal apexes 357 roughly frame distal most engagement cage 353. This characteristic is most easily seen in FIG. 30, though other features of separator 310 are obscured when the device is viewed from the perspective illustrated in FIG. 30.

Returning now to the proximal end 312 of separator 310, the features of engagement cages 350 can now be described. Just distal to proximal apexes 313 and extending from each upright 320 is a rib 335. Each rib 335 extends at angle to uprights 320 at its point of attachment thereto, or somewhat diagonally, to meet an adjacent rib 335 extending from the opposite direction. In this fashion, each rib 335 meets adjacent rib 335 to define a rib peak 317 to form an apex. Further, while other configurations are within the scope of the invention, in separator 310, also extending from each rib peak 317 is rib extension 340. As best viewed in FIG. 30, ribs 335, rib peak 317 and rib extensions 340 together define a wish-bone like configuration. This pattern repeats at each subsequent set of uprights 321, 322 and 326, defining subsequent sets of ribs 336, 337 and 338 (and apices), and corresponding rib extensions 341, 342, and 343.

Figure 32:
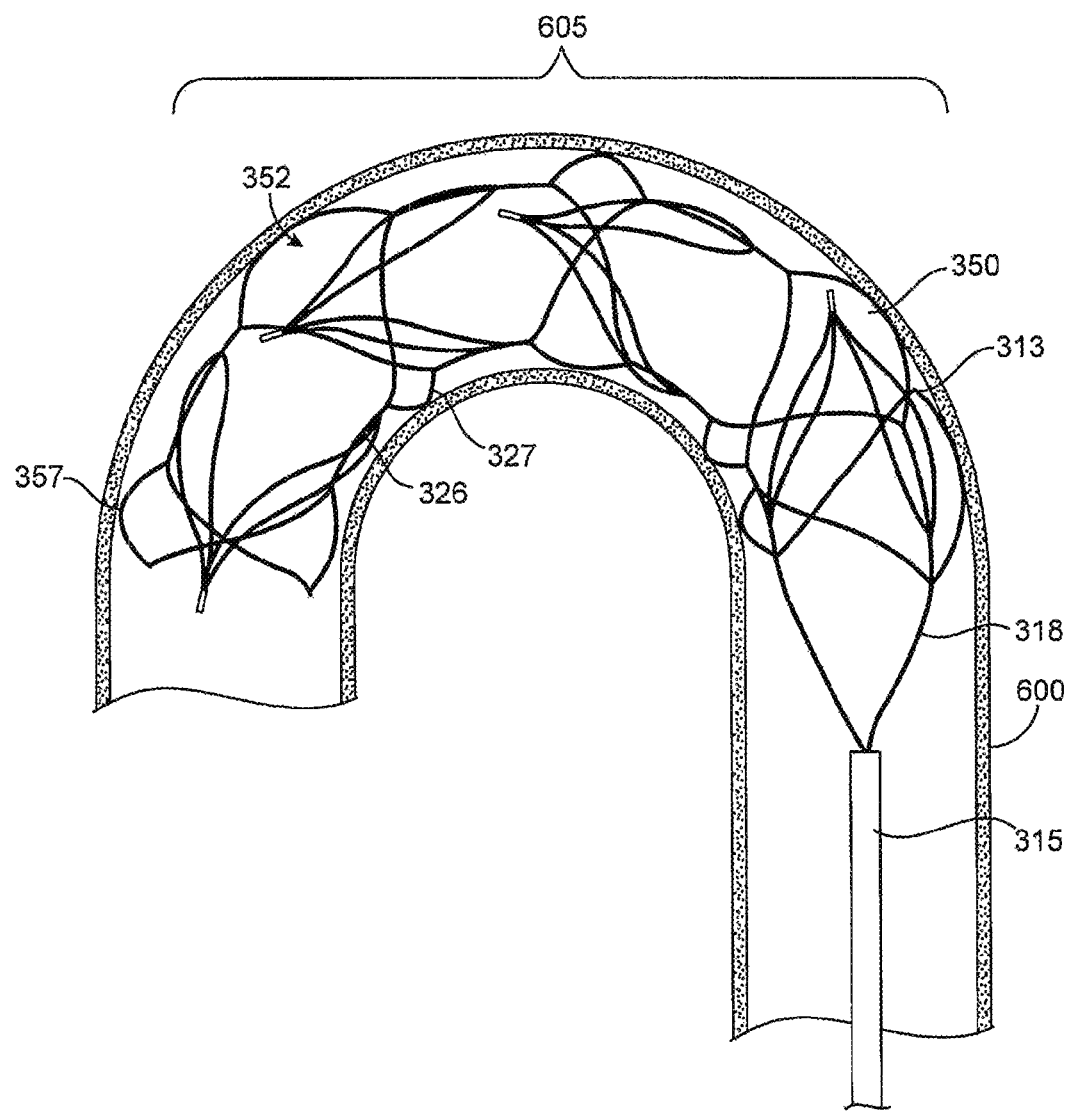
FIG. 32 is a side view of the thromboembolic separator of FIGS. 29 and 30 disposed within a curved portion of a vessel, where the vessel is shown in cross section.

During the manufacture of the finished separator 310 illustrated in FIGS. 29 and 30, each rib extension 340, 341 and 343 is biased into central lumen 330 until it meets the respective rib extension 340, 341, or 343 approaching from the opposite side of separator 310. Each rib extension 340, 341, 342, and 343 thereby biases each rib 335, 336, 337, and 338 somewhat into central lumen 330. Each rib extension 340, 341, 342, and 343 is then mated with its opposing rib extension 340, 341, 342 or 343, and attached thereto via a rib extension joiner 345, 346, 348 or 349, though other suitable means of attachment are within the scope of the invention. Ribs 335, 336, 337 and 338, together with rib extensions 340, 341, 342 and 343 thereby form engagement cages 350, 351, 352 and 353, disposed within central lumen 330. Separator 310 is shown having four such engagement cages 350, 351, 352, and 353 but a device according to the invention may have a greater or a lesser number. For example, FIG. 32 illustrates an alternate embodiment, in which only the proximal most and distal most rib extensions are attached within the central lumen. The intermediate rib extensions remain unattached, leaving opposing rib peaks generally flush with the "walls" of the device. The separator illustrated in FIG. 32 will be discussed in greater detail below.

Prior to delivery and deployment of separator 310, separator 310 will be collapsed, crimped down or otherwise reduced to its delivery configuration and restrained therein by a sheath (not shown). In preparation for treating a subject, the device within its sheath will be loaded in a delivery catheter. During a procedure performed under fluoroscopic visualization, the delivery catheter is tracked to the site of the occlusion. The distal end of the catheter is tracked through the occlusion until the distal tip thereof extends beyond the occlusion. In a slight variation of the methods described above in relation to alternate embodiments, separator 310 is preferably positioned inside a thrombus prior to deployment, and advantageously will be of a length that is greater than the length of the thrombus.

At this point, the thromboembolic separator 310 is deployed from the distal end of a delivery and aspiration catheter. The sheath (not pictured) is then withdrawn to allow partial or complete expansion of the separator within the vessel. When the sheath is withdrawn to allow expansion of separator 310, the separator 310 engages a thromboembolism in a vessel. The sheath can then be advanced over thromboembolic separator 310, which readily collapses back into the sheath. A large portion or all of the thromboembolism is thereby removed from the vessel and into the catheter. Additional therapeutics, such as pharmacologic agents, may be administered before and/or during deployment if desired by the physician. In addition, or alternatively, additional mechanical means for removal of thromboembolic material may be deployed while the separator is in place within the lumen. Further, expansion of the separator may be increased incrementally during use. And, contrast die may be injected at any point during deployment of the separator to determine the extent of restoration of blood flow.

To augment the ability to remove a thromboembolism, in a fashion similar to that described above in connection with other embodiments, an aspiration pump may be activated to establish negative pressure within the delivery and aspiration catheter. In this fashion, negative pressure will be created within the cerebral artery and exerted upon the thromboembolism. To further augment the ability to remove the thromboembolism, or in the instance the aspiration pump does not adequately draw all or most of the thromboembolism into the catheter, the delivery sheath may be advanced over at least a portion of the separator and into contact with a portion of the thromboembolism, at least at the proximal end of the separator. This will serve to break up, soften, and/or clear thromboembolic material that is blocking aspiration.

Advancing and retracting the sheath repeatedly also serves to remove any clogs or flow restrictions within the lumen of the delivery and aspiration catheter during the aspiration due to the passage of thromboembolic material through the lumen of the delivery and aspiration catheter. In either event, the aspiration pump will draw or bias the thromboembolic fragments or the softened thromboembolism into the aspiration catheter. The thromboembolic separator and delivery and aspiration catheter may then be withdrawn such that the separator and aspiration catheter remove the thromboembolism from the patient.

As described above, separator 310 is preferably positioned within a thromboembolism prior to deployment. In some instances, the thromboembolism is located within a curved vessel, and separator 310 will be deployed within a curved vessel. Clear advantages of separator 310 are illustrated in FIG. 32, in which separator 310 is shown deployed in a curved vessel model 600. When deployed within a curved tubular vessel, separator 310 resists kinking and collapsing. Further, separator 310 may be partially or fully withdrawn into a delivery sheath (not pictured) without kinking or collapsing, repositioned and redeployed. Some portions of separator 310 may expand into contact with the surrounding walls of the vessel. More specifically, near the proximal end of separator 310, proximal apexes 313 may expand into contact with the vessel wall, depending upon vessel size and morphology. Near the distal end of separator 310, distal apexes 357 expand and may or may not contact with the vessel wall. Some, all, or portions of some or all of arms 323, 325 and 327, forks 330, 332 and 334, and uprights 320, 321, 322 and 326 may also contact the vessel wall. As shown in FIG. 32 within model vessel 600, separator 310 generally conforms to the curvature or bend 605 of the vessel. Engagement cages 350, 351, 352 and 353 may remain disposed more or less within the central lumen 330, depending upon the degree of curvature of the vessel, vessel morphology, placement of the length of separator 310 with respect to the curvature 605, and other factors. For example, as illustrated in FIG. 32, portions of some engagement cages 350, 351, 352 and 353 may be disposed in close proximity to the vessel wall. In any event, the function of the engagement cages 350, 351, 352 and 353 is to engage embolic material in order to remove it from the vessel. When in actual use by the physician, the separator may be completely resheathed and removed from the vessel when desired. Advancement of the sheath and/or retraction of separator 310 will cause separator 310 to return to its collapsed configuration within the sheath. Embolic material will remain engaged to engagement cages 350, 351, 352 and 353, and will consequently also be removed from the vessel, thereby helping to restore blood flow to the vessel. Additional treatment, whether pharmacologic or mechanical, may continue or commence according to the treating practitioners' determination.

Figure 33:
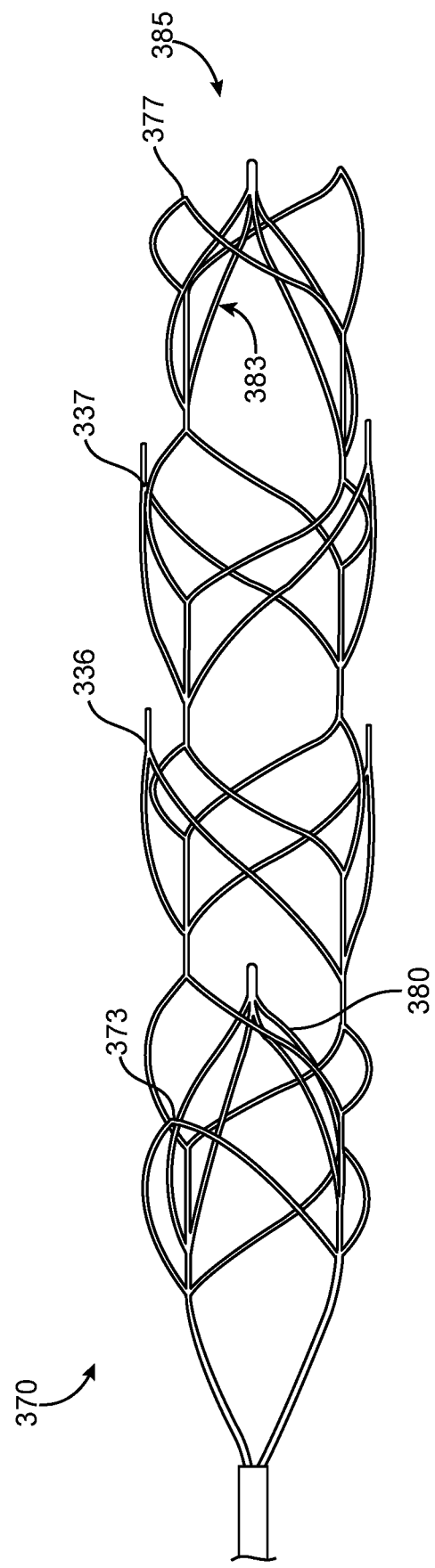
FIG. 33 is a perspective view of an alternate thromboembolic separator. The separator of FIG. 33 has the cut pattern illustrated in FIG. 31, but it is finished in a manner that is slightly different than the method used to finish the separator of FIGS. 29 and 30.

FIG. 33 illustrates an embodiment according to the invention that is similar to that described in FIGS. 29-32, with a few important distinctions. A significant distinction of separator 370 from separator 310 is that separator 370 includes only two engagement cages 380 and 383. The cut pattern for manufacture of separator 370 of FIG. 32 is the same pattern as that illustrated in FIG. 31. Further, the process of manufacturing separator 370 is the same as that used to manufacture separator 310 except for a few finishing steps. More specifically, in constructing the finished device from pattern 311, only the proximal-most set of rib extensions 340 and the distal-most set of rib extensions 343 are biased into central lumen 385 and attached to one another to form engagement cages 380 and 383. Ribs 336 and 337 remain unattached to adjacent ribs and are part of the outer diameter of deployed device 370. And because each set is oriented at roughly 90° to each subsequent set, unattached ribs 335 have generally the same orientation as distal apexes 377, and unattached ribs 337 lie generally oriented with proximal apexes 373. The methods of manufacture and methods of use of separator 370 are otherwise generally the same as those methods described above in relation to FIGS. 29-32.

Figure 34:
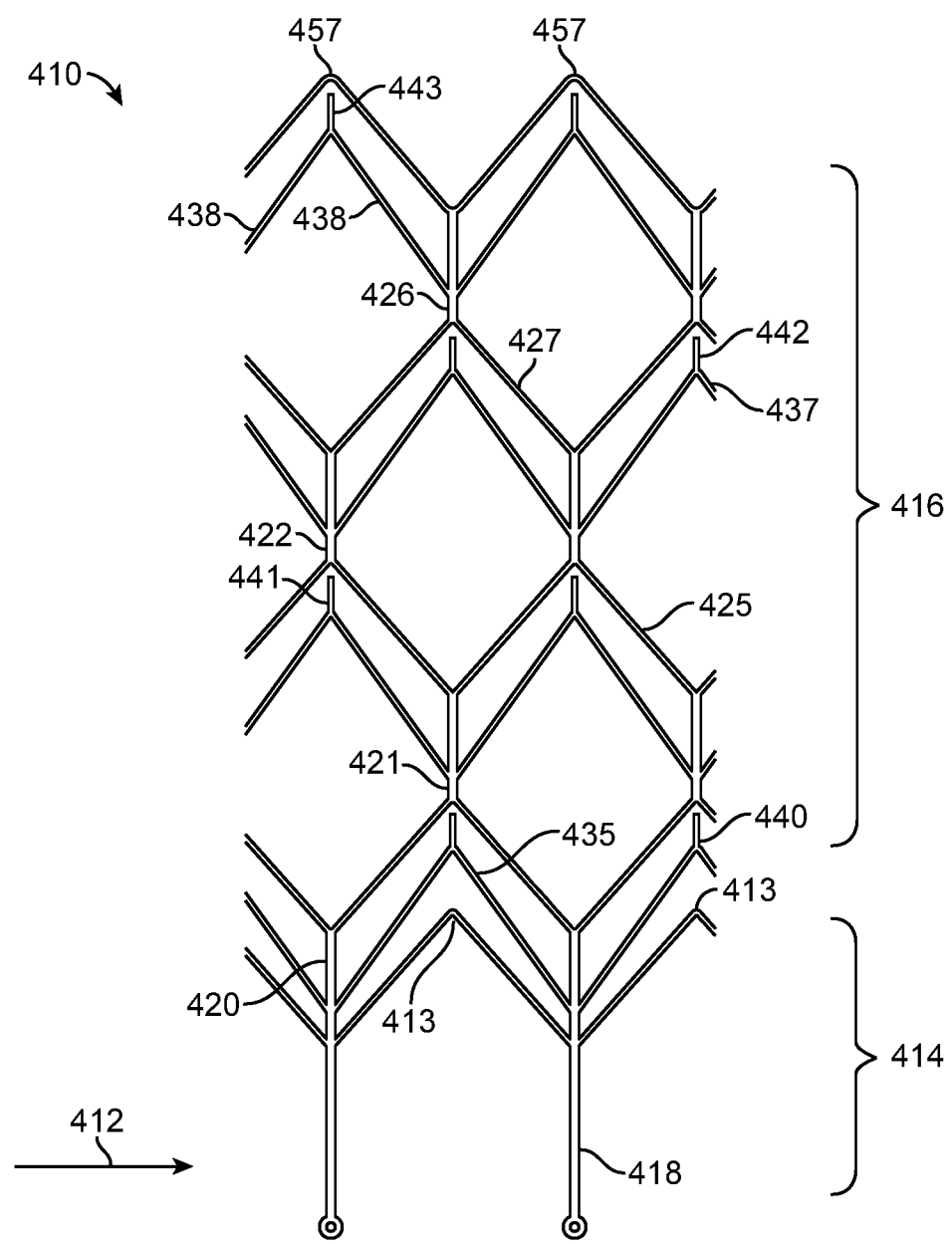
FIG. 34 is a plan view of an alternate cut pattern for a thromboembolic separator. Although a resulting thromboembolic separator formed from the pattern of FIG. 34 is preferably a generally tubular structure.

An alternate thromboembolic separator according to the invention may be constructed using a cut pattern as illustrated in FIG. 34. In the pattern 410 of FIG. 34, proximal end 412 includes legs 418. When in its final form, a thromboembolic separator manufactured from pattern 410 will be mounted at its proximal end 412, to a pusher (not pictured) via legs 418. Legs 418 extend distally from the proximal end 412 to form a first set of uprights 420. A row of proximal apexes 413 is attached to uprights 420. In a finished device, proximal apexes 413 will surround a central lumen, and further define the base 414 of a separator constructed from pattern 410.

Proceeding distally from proximal apexes 413, and ignoring ribs 435, each upright 420 divides in a Y-like fashion and extends substantially diagonally to form a first set of arms 423. Each arm 423 extends diagonally to join an adjacent arm 423 at a fork 440. From each fork 440, a second set of uprights 421 extends. This pattern repeats until the distal end of cut pattern 410. The body 416 of pattern 410 is thus defined primarily by successive sets of uprights 420, 421, 422, and successive sets of arms 423, 425, 427, where the number of both sets can vary according to the invention. Uprights 420, 421, 422, and arms 423, 425, 427 will "surround", or be disposed about, a central axis of a finished device. The distal end of pattern 420 is defined by distal apexes 457, which will also surround a central axis of a finished device.

Returning now to the proximal end 412 of pattern 410, the features of wishbone elements 450 can now be described. Just distal to proximal apexes 413 and similarly extending from each upright 420 is a rib 435. Each rib 435 extends at an angle to an upright, or somewhat diagonally to meet an adjacent rib 435 extending from the opposite direction. In this fashion, each rib 435 meets adjacent rib 435 to define a rib peak 415. Further, extending from each rib peak 415 is rib extension 440. Ribs 435, rib peaks 415 and rib extensions 440 together define wish-bone like configurations, referred to here as wishbone elements 450. This pattern repeats at each subsequent set of uprights 421 and 422, defining subsequent sets of ribs 436, 437 and 438, and corresponding rib extensions 441, 442, and 443.

In order to manufacture of a finished separator from pattern 410, some or all of rib extensions 440, 441 and 443 will be biased into a central lumen until it meets the respective rib extension 440, 441, or 443 approaching from the opposite side. Some or all of rib extensions 440, 441, 442, and 443 will then be mated with its opposing rib extension and attached thereto. Some or all of ribs 435, 436, 437 and 438, together with some or all of rib extensions 440, 441, 442 and 443 will thereby form engagement cages disposed within a central lumen of the finished device.

Figure 35:
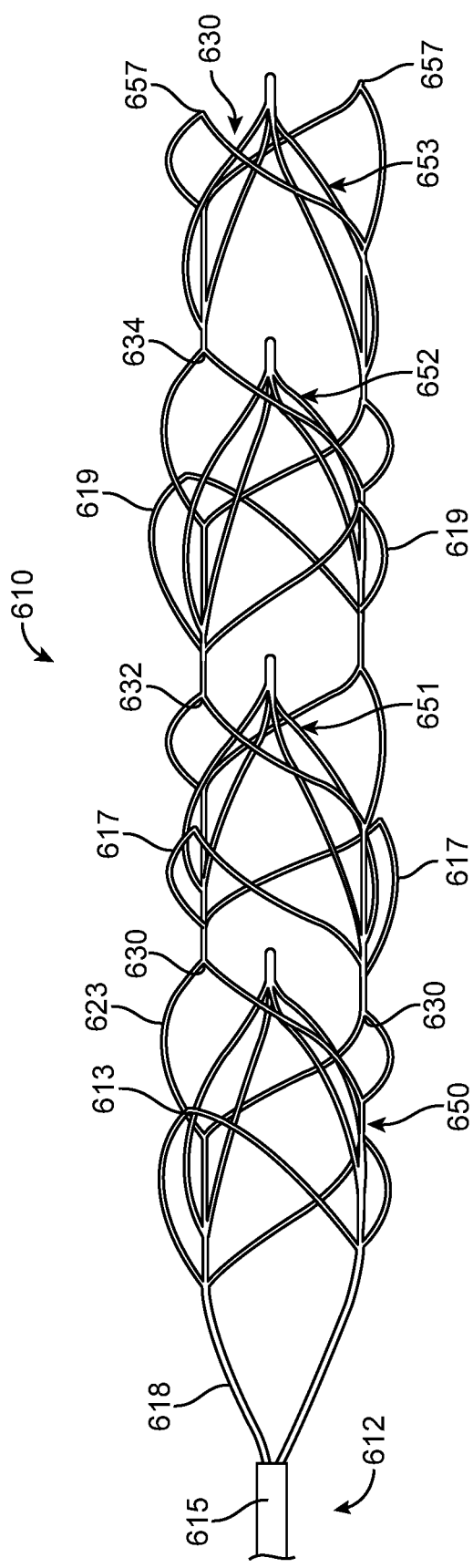
FIG. 35 is a perspective view of yet another alternative embodiment of a thromboembolic separator according to the invention.
Figure 36:
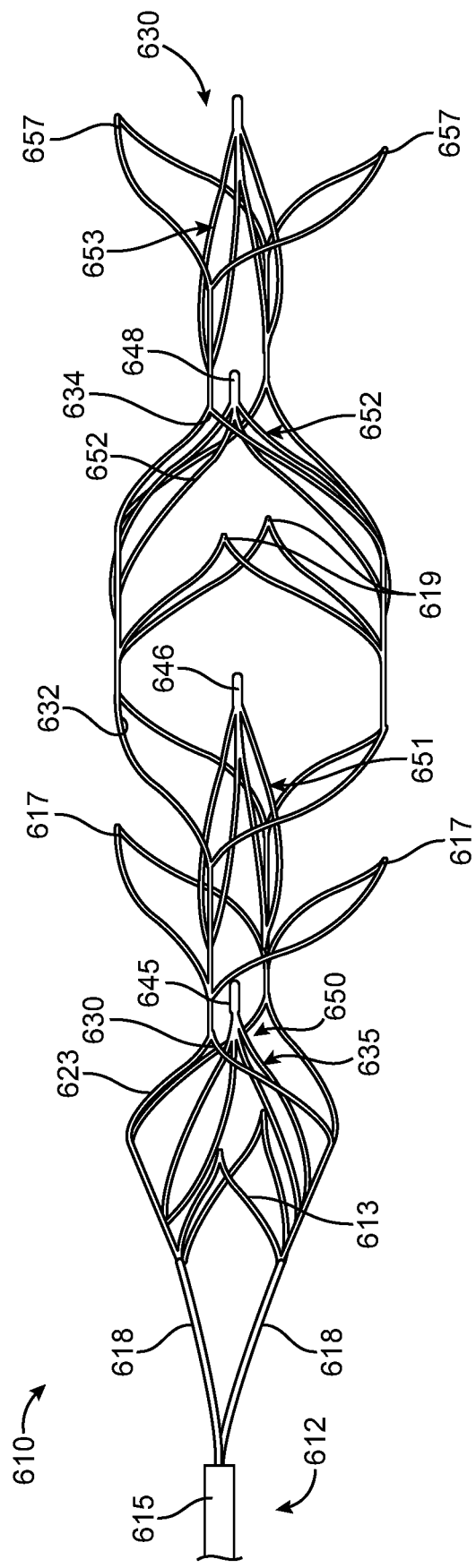
FIG. 36 is an alternate perspective view of the thromboembolic separator of FIG. 35. The thromboembolic separator of FIG. 35 is rotated slightly to reveal the perspective view of FIG. 36.
Figure 37:
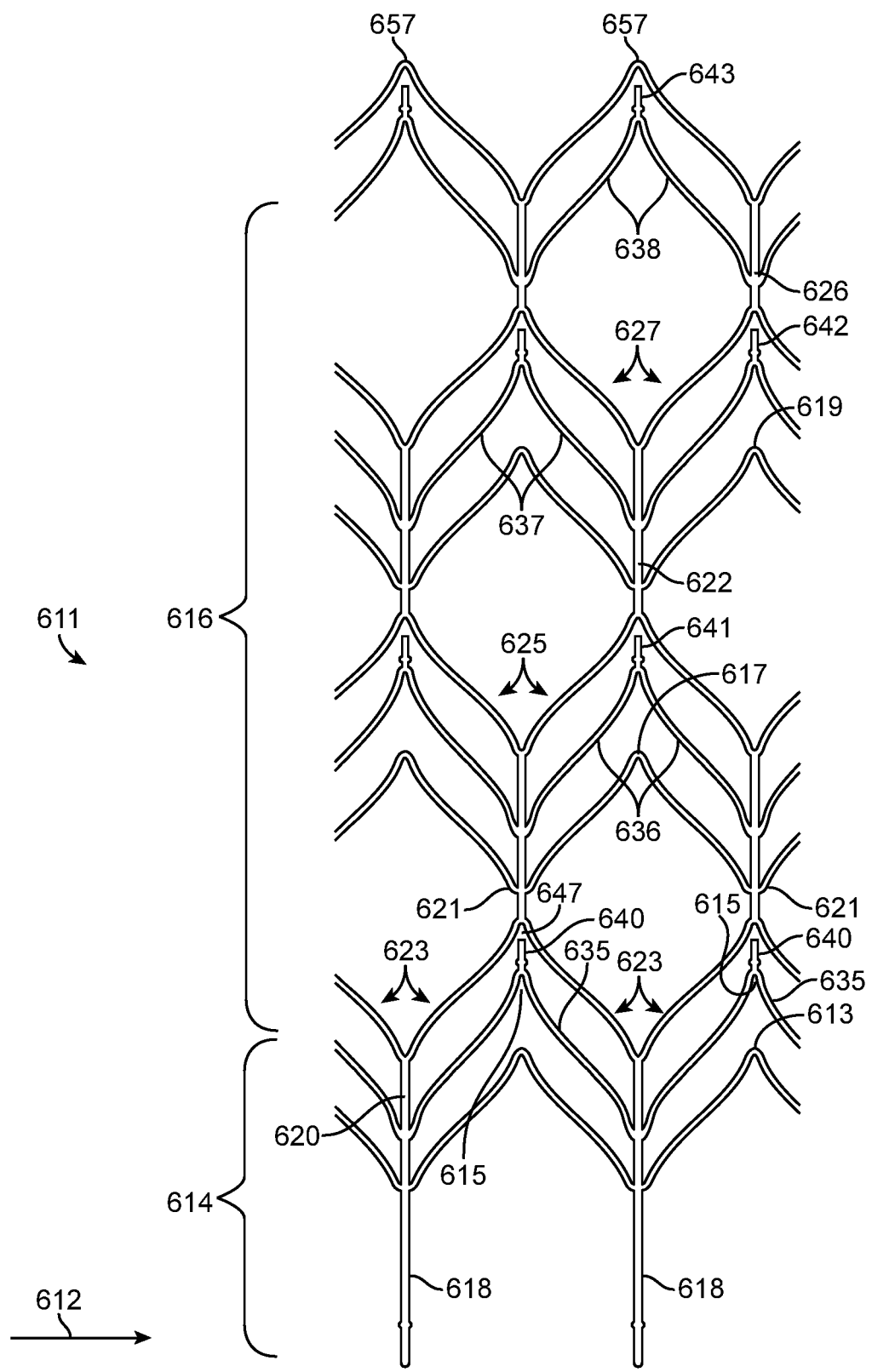
FIG. 37 is a plan view or rolled out of the cut pattern of the thromboembolic separator of FIGS. 35 and 36. Although the separator is preferably a generally abstract tubular structure.

Turning now to yet another alternative embodiment according to the invention, separator 610 is shown in its deployed configuration in FIGS. 35 and 36. The flat pattern 611 cut to manufacture separator 610 is illustrated in FIG. 37. The pattern 611 used to manufacture separator 610 is similar to that illustrated in FIG. 31 and described above, with one primary distinction. Pattern 611 includes first body apexes 617 and second body apexes 619, in addition to proximal apexes 613 and distal apexes 657. Seen easily in FIG. 36 in a separator 610 illustrated in its deployed configuration, proximal apexes 613, first body apexes 617, second body apexes 619 and distal apexes 657 represent successive sets of apexes. And although other suitable configurations are within the scope of the invention, in deployed separator 610, each successive set of apexes is oriented at roughly 90° to the preceding set of apexes.

Separator 610 is otherwise very similar to those described above. Separator 610 when deployed may be between 18-22 mm or other suitable length, but in this example is approximately 20 mm. Separator 610 is mounted to pusher 615 via legs 618. Separator 610 includes four engagement cages 650, 651, 652 and 653, but may according to the invention include a greater or lesser number. Engagement cages 650, 651, 652 and 653 engage embolic material in a vessel of a subject during use of separator 610.

Returning to FIG. 37, and beginning at its proximal end 612, legs 618 extend distally to form a first set of uprights 620. Proximal apexes 613 are attached to uprights 620. (Proximal apexes 613 cup slightly in a deployed separator 610 to partially define a central lumen 630.) Base 614 of separator 610 is thus defined by legs 618, uprights 620, and proximal apexes 613. Proceeding distally from proximal apexes 613, and ignoring ribs 635 and engagement cages 650-653 for now, the distal end of each upright 620 divides in a Y-like fashion to form a first set of arms 623. Each arm 623 extends generally diagonally to join an adjacent arm 623 at a fork 630. From fork 630, a second set of uprights 621 extends. This pattern repeats until the distal end of pattern 611 or separator 610. The body 616 of separator 610 is thus defined primarily by first body apexes 617, second body apexes 619, successive sets of arms 623, 625 and 627, forks 630, 632 and 634, and successive sets of uprights 620, 621, 622 and 626, though a greater or lesser number of sets is within the scope of the invention. In deployed separator 610 shown in FIGS. 36 and 37, apexes 613, 617, 619, 657, arms 623, 625 and 627, forks 630, 632 and 634, and uprights 620, 621, 622, 626 skeletally frame the engagement cages and define a central lumen 630. Proximal apexes 613, first body apexes 617, second body apexes 619 and distal apexes 657 in the deployed separator 610 cup slightly, and each successive set of apexes is oriented at roughly 90° to its preceding set of apexes.

Turning now to the proximal end 612 of separator 610 and pattern 611, the features of engagement cages 650 can now be described. Just distal to proximal apexes 613 and similarly extending from each upright 620 is a rib 635. Each rib 635 extends somewhat diagonally to meet an adjacent rib 635 extending from the opposite direction. In this fashion, each rib 635 meets adjacent rib 635 to define a rib peak 615. Further, extending from each rib peak 615 is rib extension 640. As best viewed in FIG. 36, ribs 635, rib peaks 615 and rib extensions 640 together define a wish-bone like configuration. This pattern repeats at each subsequent set of uprights 621, 622 and 626, defining subsequent sets of ribs 636, 637 and 638, and corresponding rib extensions 641, 642, and 643.

During the manufacture of the finished separator 610 illustrated in FIGS. 36 and 37, each rib extension 640, 641 and 643 is biased into central lumen 630 until it meets the respective rib extension 640, 641, or 643 approaching from the opposite side of separator 610. Each rib extension 640, 641, 642, and 643 thereby biases each rib 635, 636, 637, and 638 somewhat into central lumen 630. Each rib extension 640, 641, 642, and 643 is then mated with its opposing rib extension 640, 641, 642 or 643, and attached thereto via a rib extension joiner 645, 646, 648 or 649, though other suitable means of attachment are within the scope of the invention. Ribs 635, 636, 637 and 638, together with rib extensions 640, 641, 642 and 643 thereby form engagement cages 650, 651, 652 and 653, disposed within central lumen 630. Separator 610 is shown having four such engagement cages 650, 651, 652, and 653 but a device according to the invention may have a greater or a lesser number.

Prior to delivery and deployment of separator 610, separator 610 will be collapsed, crimped down or otherwise reduced to its delivery configuration and restrained therein by a sheath (not shown). In preparation for treating a subject, the device within its sheath will be loaded in a delivery catheter. During a procedure performed under fluoroscopic visualization, the delivery catheter is tracked to the site of the occlusion. The distal end of the catheter is tracked through the occlusion until the distal tip thereof extends beyond the occlusion. In a slight variation of the methods described in relation to FIGS. 25-28, separator 610 is preferably positioned inside a thrombus prior to deployment, and advantageously will be of a length that is greater than the length of the thrombus.

The delivery catheter or sheath (not pictured) is then withdrawn to allow partial or complete expansion of the separator within the vessel. Additional therapeutics, such as pharmacologic agents, may be administered before and/or during deployment if desired by the physician. In addition, or alternatively, additional mechanical means for removal of thromboembolic material may be deployed while the separator is in place within the lumen. Further, expansion of the separator may be increased incrementally during use. And, contrast die may be injected at any point during deployment of the separator to determine the extent of restoration of blood flow.

When deployed within a tubular vessel, portions of separator 610 may contact the surrounding walls of the vessel, depending upon vessel size and morphology. More specifically, in addition to contact via the apexes described above, separator 610 may also contact the vessel wall via all or portions of arms 623, 625 and 627 and uprights 620, 621, 622 and 626. Engagement cages 650, 651, 652 and 653 may remain disposed more or less within the central lumen 330, depending upon the degree of curvature of the vessel, vessel morphology, placement of the length of separator 610 with respect to a curvature within a vessel, and other factors. In any event, the function of the engagement cages 650, 651, 652 and 653 is to engage embolic material in order to remove it from the vessel. When in actual use by the physician, the separator may be resheathed and removed from the vessel when desired. Retraction of separator 610 will cause separator 610 to return to its collapsed configuration within the sheath (not pictured). Embolic material will remain engaged to engagement cages 650, 651, 652 and 653 and consequently also be removed from the vessel, thereby helping to restore blood flow to the vessel. Additional treatment, whether pharmacologic or mechanical, may continue or commence according to the treating practitioners' determination.

While the invention may be modified and alternative forms may be used, specific embodiments of the invention have been illustrated and described in detail. It should be understood, however, that the description herein of specific embodiments is not intended to limit the invention to the particular forms disclosed. The invention and following claims are intended to cover all modifications and equivalents falling within the spirit and scope of the invention.

What is claimed is:

1. A method of manufacture of a system for removal of thromboembolic material from a blood vessel, the method comprising the steps of:
    cutting a plurality of uprights and apexes from a length of tubing to form a separator element with a lumen, a proximal end, and a distal end;
    adjoining some of the apexes to one another to form three or more cages, wherein each cage forms an internal apex that is centrally disposed within the lumen and is pointed towards the distal end; and
    mounting said separator element to an elongate element.

2. The method according to claim 1, wherein the step of cutting a plurality of uprights and apexes further comprises cutting said uprights generally parallel to one another throughout the length of the tubing, and cutting said apexes so that they extend at an angle to the uprights.

3. The method according to claim 1, wherein the step of cutting the apexes further comprises cutting the apexes in the wall of the tubing opposite one another.

4. The method according to claim 1, wherein the step of cutting the apexes further comprises cutting apex extensions.

5. The method according to claim 1, wherein the step of cutting the uprights and apexes further comprises cutting some of the apexes intermediate the length of the uprights.

6. The method according to claim 1, wherein the step of mounting the separator element further comprises mounting the separator element to the elongate element via one or more of the uprights.

7. The method according to claim 1, wherein the step of cutting the apexes comprises cutting a series of pairs of apexes along a longitudinal axis of the tubing, wherein each pair of apexes is oriented at 90° around the axis to each subsequent pair of apexes.

* * * * *